United States Patent
Pappas et al.

(10) Patent No.: US 11,315,663 B2
(45) Date of Patent: *Apr. 26, 2022

(54) SYSTEMS AND METHODS FOR PRODUCING PERSONAL CARE PRODUCTS

(71) Applicant: Colgate-Palmolive Company, New York, NY (US)

(72) Inventors: Iraklis Pappas, Pennsauken, NJ (US); Bartosz Luczynski, Dover, NJ (US); Donghui Wu, Bridgewater, NJ (US); Dong Hyun Kim, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/949,465

(22) Filed: Oct. 30, 2020

(65) Prior Publication Data

US 2021/0151130 A1 May 20, 2021

Related U.S. Application Data

(63) Continuation of application No. 16/731,533, filed on Dec. 31, 2019, now Pat. No. 10,861,588, which is a
(Continued)

(51) Int. Cl.
*G16C 20/30* (2019.01)
*G16C 20/70* (2019.01)
*G16C 20/10* (2019.01)

(52) U.S. Cl.
CPC ............. *G16C 20/30* (2019.02); *G16C 20/10* (2019.02); *G16C 20/70* (2019.02)

(58) Field of Classification Search
CPC .................................................... G16C 20/30
(Continued)

(56) References Cited

U.S. PATENT DOCUMENTS

| 1,005,571 A | 10/1911 | Parker |
| 1,009,398 A | 11/1911 | Flenniken |

(Continued)

FOREIGN PATENT DOCUMENTS

| CN | 101477597 | 7/2009 |
| CN | 107679362 | 2/2018 |

(Continued)

OTHER PUBLICATIONS

Hada et al., 2017, "Mixture formulation through multivariate statistical analysis of process data in property cluster space," Computers & Chemical Engineering 107:26-36.
(Continued)

*Primary Examiner* — Ricky Go

(57) ABSTRACT

A system, apparatus, and/or method is disclosed for producing a personal care product. An identity of a considered chemical composition may be input into a model (e.g., a machine learning model). The identity of the considered chemical composition may include ingredients. Each of the ingredients of the considered chemical composition may be associated with a value of a chemoinformatic property of chemoinformatic properties of the considered chemical composition. A value of the property of the considered chemical composition may be determined via the model. The value may be based on the identity of the considered chemical composition. The property of the considered chemical composition may be affected by an interaction of at least two of the ingredients of the considered chemical composition. A personal care product comprised of the considered chemical composition may be produced.

20 Claims, 19 Drawing Sheets

Related U.S. Application Data continuation of application No. 16/672,922, filed on Nov. 4, 2019, now Pat. No. 10,839,941, which is a continuation of application No. 16/452,214, filed on Jun. 25, 2019, now Pat. No. 10,515,715.

(58) Field of Classification Search
USPC .......................................................... 702/30
See application file for complete search history.

(56) References Cited

U.S. PATENT DOCUMENTS

| | | | |
|---|---|---|---|
| 5,434,796 | A | 7/1995 | Weininger |
| 5,526,281 | A | 6/1996 | Chapman et al. |
| 5,854,992 | A | 12/1998 | Shakhnovich et al. |
| 6,434,490 | B1 | 8/2002 | Agrafiotis et al. |
| 6,442,536 | B1 | 8/2002 | Akhras et al. |
| 6,571,226 | B1 | 5/2003 | Mydlowec et al. |
| 6,647,341 | B1 | 11/2003 | Golub et al. |
| 6,807,491 | B2 | 10/2004 | Pavlovic et al. |
| 6,834,239 | B2 | 12/2004 | Lobanov et al. |
| 7,047,137 | B1 | 5/2006 | Kasif et al. |
| 7,136,759 | B2 | 11/2006 | Kangas et al. |
| 7,194,359 | B2 | 3/2007 | Duffy et al. |
| 7,430,475 | B2 | 9/2008 | Imoto et al. |
| 7,444,308 | B2 | 10/2008 | Guyon et al. |
| 7,526,415 | B2 | 4/2009 | Shan et al. |
| 7,542,947 | B2 | 6/2009 | Guyon et al. |
| 7,642,079 | B2 | 1/2010 | Cayouette et al. |
| 7,702,465 | B2 | 4/2010 | Lasters et al. |
| 7,702,467 | B2 | 4/2010 | Duffy |
| 7,702,595 | B2 | 4/2010 | Shibuya |
| 7,734,423 | B2 | 6/2010 | Crowley, Jr. et al. |
| 7,747,547 | B1 | 6/2010 | Buturovic et al. |
| 7,783,428 | B2 | 8/2010 | Gustafsson et al. |
| 7,801,685 | B2 | 9/2010 | Ho |
| 7,805,282 | B2 | 9/2010 | Casey et al. |
| 7,856,321 | B2 | 12/2010 | Lanza et al. |
| 7,894,995 | B2 | 2/2011 | Jojic et al. |
| 7,921,068 | B2 | 4/2011 | Guyon et al. |
| 7,991,557 | B2 | 8/2011 | Liew et al. |
| 7,996,156 | B2 | 8/2011 | Beger et al. |
| 8,005,620 | B2 | 8/2011 | Gustafsson et al. |
| 8,005,626 | B2 | 8/2011 | Kelkar et al. |
| 8,019,699 | B2 | 9/2011 | Baxter |
| 8,185,321 | B2 | 5/2012 | Sakakibara et al. |
| 8,229,872 | B2 | 7/2012 | Gilhuly |
| 8,296,300 | B2 | 10/2012 | Kwon et al. |
| 8,352,390 | B2 | 1/2013 | Yuta |
| 8,386,401 | B2 | 2/2013 | Virkar et al. |
| 8,458,103 | B2 | 6/2013 | Brooks et al. |
| 8,473,448 | B2 | 6/2013 | Yuta |
| 8,814,790 | B2 | 8/2014 | Eisenhandler et al. |
| 8,862,520 | B2 | 10/2014 | Agarwal |
| 8,949,157 | B2 | 2/2015 | Okuno et al. |
| 9,002,682 | B2 | 4/2015 | Kasabov |
| 9,043,249 | B2 | 5/2015 | Russak |
| 9,218,460 | B2 | 12/2015 | Singh et al. |
| 9,367,812 | B2 | 6/2016 | Segall et al. |
| 9,483,610 | B2 | 11/2016 | McMillen et al. |
| 9,519,620 | B1 | 12/2016 | Pinel et al. |
| 9,552,462 | B2 | 1/2017 | Walters et al. |
| 9,697,556 | B2 | 7/2017 | Mazed et al. |
| 9,760,834 | B2 | 9/2017 | Chae et al. |
| 9,965,597 | B2 | 5/2018 | Becker et al. |
| 9,971,737 | B2 | 5/2018 | Pinel et al. |
| 10,102,476 | B2 | 10/2018 | Caraviello et al. |
| 10,189,616 | B2 | 1/2019 | Kraft |
| 10,216,910 | B2 | 2/2019 | Karthikeyan et al. |
| 10,249,389 | B2 | 4/2019 | Athey et al. |
| 10,332,276 | B2 | 6/2019 | Byron et al. |
| 10,339,464 | B2 | 7/2019 | Martin et al. |
| 10,360,495 | B2 | 7/2019 | Chapela et al. |
| 10,361,003 | B2 | 7/2019 | Segal et al. |
| 10,515,715 | B1 | 12/2019 | Pappas et al. |
| 2001/0049585 | A1 | 12/2001 | Gippert et al. |
| 2002/0077754 | A1 | 6/2002 | McGregor et al. |
| 2002/0090631 | A1 | 7/2002 | Gough et al. |
| 2002/0187514 | A1 | 12/2002 | Chen et al. |
| 2003/0162219 | A1 | 8/2003 | Sem et al. |
| 2004/0115726 | A1 | 6/2004 | Nagashima et al. |
| 2005/0240355 | A1 | 10/2005 | Brown et al. |
| 2005/0278124 | A1 | 12/2005 | Duffy et al. |
| 2005/0288871 | A1* | 12/2005 | Duffy ................... G16C 20/70 702/27 |
| 2006/0031027 | A1 | 2/2006 | Alman |
| 2006/0074824 | A1 | 4/2006 | Li |
| 2006/0200320 | A1 | 9/2006 | Al-Murrani |
| 2006/0210967 | A1 | 9/2006 | Agan et al. |
| 2006/0253262 | A1 | 11/2006 | Ching et al. |
| 2009/0024375 | A1 | 1/2009 | Kremer et al. |
| 2009/0024547 | A1 | 1/2009 | Lu et al. |
| 2010/0010946 | A1 | 1/2010 | De Winter et al. |
| 2010/0121791 | A1 | 5/2010 | Kang et al. |
| 2010/0234246 | A1 | 9/2010 | Jung et al. |
| 2010/0280895 | A1 | 11/2010 | Mottola |
| 2011/0224913 | A1 | 9/2011 | Cui et al. |
| 2011/0257893 | A1 | 10/2011 | Taylor et al. |
| 2011/0305648 | A1 | 12/2011 | Knapek et al. |
| 2012/0158389 | A1 | 6/2012 | Wu et al. |
| 2012/0239309 | A1* | 9/2012 | Russak ................ G16C 20/70 702/30 |
| 2013/0041683 | A1 | 2/2013 | Boissel |
| 2013/0089838 | A1 | 4/2013 | Adkins et al. |
| 2013/0144584 | A1 | 6/2013 | Chen et al. |
| 2013/0303387 | A1 | 11/2013 | Sander et al. |
| 2014/0039913 | A1 | 2/2014 | Sandholm |
| 2014/0236548 | A1 | 8/2014 | Conduit et al. |
| 2014/0255882 | A1 | 9/2014 | Hadad et al. |
| 2015/0134315 | A1 | 5/2015 | Sarmiento et al. |
| 2015/0220838 | A1 | 8/2015 | Martin et al. |
| 2015/0242566 | A1 | 8/2015 | Samer |
| 2015/0310162 | A1 | 10/2015 | Okuno et al. |
| 2016/0086087 | A1 | 3/2016 | Ghouti |
| 2016/0103949 | A1 | 4/2016 | Benz et al. |
| 2016/0131603 | A1 | 5/2016 | Van Der Mei et al. |
| 2016/0132631 | A1 | 5/2016 | Bremel et al. |
| 2016/0140452 | A1 | 5/2016 | Garcia Sedano et al. |
| 2017/0039314 | A1 | 2/2017 | Bremel et al. |
| 2017/0068777 | A1 | 3/2017 | Parnell et al. |
| 2017/0161635 | A1 | 6/2017 | Oono et al. |
| 2017/0204447 | A1 | 7/2017 | Rickard et al. |
| 2017/0329892 | A1 | 11/2017 | Fan et al. |
| 2017/0344892 | A1 | 11/2017 | Byron et al. |
| 2017/0372197 | A1 | 12/2017 | Baughman et al. |
| 2018/0004905 | A1 | 1/2018 | Szeto |
| 2018/0075369 | A1 | 3/2018 | Calmon et al. |
| 2018/0121826 | A1 | 5/2018 | Nugent |
| 2018/0172667 | A1 | 6/2018 | Noskov et al. |
| 2018/0189636 | A1 | 7/2018 | Chapela et al. |
| 2018/0240359 | A1 | 8/2018 | Hujsak |
| 2018/0247227 | A1 | 8/2018 | Holtham |
| 2018/0253454 | A1* | 9/2018 | Botea ................... G16C 20/50 |
| 2018/0286516 | A1 | 10/2018 | Menichetti et al. |
| 2018/0293501 | A1 | 10/2018 | Ambati et al. |
| 2018/0307804 | A1 | 10/2018 | Dey et al. |
| 2018/0307805 | A1 | 10/2018 | Dey et al. |
| 2018/0308143 | A1 | 10/2018 | Chan et al. |
| 2019/0251455 | A1 | 8/2019 | Spangler et al. |

FOREIGN PATENT DOCUMENTS

| | | |
|---|---|---|
| CN | 107918718 | 4/2018 |
| CN | 108268893 | 7/2018 |
| EP | 2381381 | 10/2011 |
| EP | 3206145 | 8/2017 |
| IN | 201721044239 | 8/2018 |
| JP | 2016-012247 | 1/2016 |
| KR | 20180022159 | 3/2018 |
| KR | 101864252 | 6/2018 |
| WO | 1994/028504 | 12/1994 |
| WO | 2002/103954 | 12/2002 |
| WO | 2003/019140 | 3/2003 |
| WO | 2004/038602 | 5/2004 |
| WO | 2008/116495 | 10/2008 |

(56) References Cited

FOREIGN PATENT DOCUMENTS

| WO | 2009/053137 | 4/2009 |
|---|---|---|
| WO | 2012/028962 | 3/2012 |
| WO | 2015/028597 | 3/2015 |
| WO | 2015/166489 | 11/2015 |
| WO | 2017/122785 | 7/2017 |
| WO | 2017/172629 | 10/2017 |
| WO | 2018/132752 | 7/2018 |
| WO | 2018/162778 | 9/2018 |
| WO | 2018/170035 | 9/2018 |
| WO | 2018/208360 | 11/2018 |

OTHER PUBLICATIONS

International Search Report and the Written Opinion of the International Searching Authority issued in International Application PCT/US2020/070111 dated Dec. 9, 2020.

Lee et al., 2014, "A knowledge-based ingredient formulation system for chemical product development in the personal care industry," Computers & Chemical Engineering 65:40-53.

Zhang et al., 2017, "An integrated framework for designing formulated products," Computers & Chemical Engineering 107:61-76.

Clercq, Marlies De, Prediction of Ingredient Combinations using Machine Learning Techniques, Trends in Food Science & Technology 49 (2016), pp. 1-101.

Lowe, Derek, AI Will Not Threaten Pharma Patents—Not This Way—In The Pipeline, Independent Blog from—Publishers of Science Translational Medicine, https://blogs.sciencemag.org/pipline/archives/2018/06/27/ai-will-not-threaten-pharma-patents-not-this-way, pp. 1-19, Jun. 27, 2018.

Pekel, Kent et al., Finding the Fluoride: Examining How and Why Developmental Relationships Are the Active Ingredient in Interventions that Work, American Journal of Orthopsychiatry 88(5), https://www.researchgate.net, Jun. 2018, pp. 1-34.

Roman Przybylski* and Rui C. Zambiazi, Predicting Oxidative Stability of Vegetable Oils Using Neural Network System and Endogenous Oil Components, Journal of the American Oil Chemists' Society (JAOCS), vol. 77, No. 9, (2000), Abstract pp. 1-8.

Tripathy, Ashis et al., Electric Nose for Black Tea Quality Evaluation Using Kernel Based Clustering Approach, International Journal of Image Processing (IJIP), vol. 6: Issue (2), 2012,pp. 1-8.

Zhang, Lei et al., "A machine learning based computer-aided molecular design/screening methodology for fragrance molecules", www.elsevier.com, Computers & Engineering, vol. 115, Jul. 2018, pp. 295-308 (14 total).

* cited by examiner

100 —

| Chemical Composition | |
|---|---|
| Ingredient | Feature of Ingredient |
| Stannous Fluoride | Used to help prevent cavities, gingivitis and protect against sensitivity. |
| Glycerin | Used to help hydrate the mouth. |
| Hydrated Silica | Used as an abrasive to help clean and polish teeth. |
| Water | Dissolves substances or ingredients |
| Propylene Glycol | An emulsifier used to prevent liquids from separating. |
| PEG-12 | A humectant that helps retain moisture or dissolves other ingredients. |
| Pentasodium Triphosphate | Used as a tartar control ingredient that helps protect from stain build-up. |
| Sodium Citrate | Used to adjust pH in the product. |
| Sodium Lauryl Sulfate | Used as a solubilizing or cleansing agent. |
| Flavor | Used to freshen breath and to improve a product's taste. |
| PVP | Used as a thickening agent. |
| Microcrystalline Cellulose | Used as a thickener or stabilizer. |
| Trisodium Phosphate | Used to adjust pH in the product. |
| Zinc Oxide | Helps provide malodor control. |
| Citric Acid | Used to adjust pH of the product. |
| Zinc Citrate | Helps provide malodor control. |
| Phosphoric Acid | Used to adjust pH in the product. |
| Sodium Saccharin | Used to provide sweetness to the product. |
| Cocamidopropyl Betaine | Used as a foaming agent or thickener. |
| Carrageenan | Used as a thickening, emulsifying, gelling, or stabilizing agent. |
| Xanthan Gum | Used as a thickener or stabilizer. |
| PVM/MA Copolymer | Used to help retain active ingredients on teeth and gums. |
| Sucralose | Used to provide sweetness to the product. |
| Titanium Dioxide | Used as a thickener or stabilizer. |

FIG. 1A

| Consumer Perception Parameters of a Chemical Composition ||
|---|---|
| Color (e.g., whiteness) | Bitterness |
| Stickiness | Saltiness |
| Wetness | Sourness |
| Slipperiness | Astringent |
| Oily/Greasiness | Numbness |
| Waxiness | Thymol |
| Powdery | Prickliness |
| Pilling | Shape (e.g., integrity of shape) |
| Fragrance (e.g., fragrancy intensity | Firmness |
| Coolness (e.g., icy coolness, nasal coolness | Smoothness |
| Removable (e.g., does it easily rub off) | Transparency |
| Ease to Foam | Ease of spread |
| Dispersibility | Sliminess |
| Volume | Creaminess |
| Viscosity | Thickness |
| Particle Size | Moistness |
| Flavor (e.g., mint intensity) | Affect on skin, hair, teeth |
| Burning sensation | Peaking |
| Sweetness | Surface film |

FIG. 1B

| Unique Identifier | Description | Percent |
|---|---|---|
| ABC123 | SORBITOL | 30 - 70 |
| ABC124 | WATER | 10 - 30 |
| ABC125 | ABRASIVE SILICA | 5 - 20 |
| ABC126 | HIGH CLEANING SILICA | 5 - 20 |
| ABC127 | GLYCERIN | 1 - 10 |
| ABC128 | POLYETHYLENE GLYCOL 600 | 1 - 5 |
| ABC129 | TETRASODIUM PYROPHOSPHATE | 1 - 5 |
| ABC130 | FLAVOR | 0.1 - 3 |
| ABC131 | THICKENING SILICA | 0.5 - 3 |
| ABC132 | SODIUM LAURYL SULFATE | 0.5 - 3 |
| ABC133 | COCAMIDOPROPYL BETAINE | 0.5 - 3 |
| ABC134 | ZINC ION SOURCE | 0.1 - 2 |
| ABC135 | MICROCRYSTALLINE CELLULOSE | 0.1 - 2 |
| ABC136 | TRISODIUM CITRATE DIHYDRATE | 0.1 - 2 |
| ABC137 | SODIUM CMC | 0.1 - 2 |
| ABC138 | FLUORIDE ION SOURCE | 0.1 - 1 |
| ABC139 | TITANIUM DIOXIDE COATED MICA | 0.1 - 2 |
| ABC140 | SODIUM SACCHARIN | 0.1 - 1 |
| ABC141 | XANTHAN GUM | 0.1 - 1 |
| ABC142 | CITRIC ACID | 0.1 - 1 |

FIG. 2B

Functions

| | |
|---|---|
| Abrasives | Emulsion Stabilizers | Propellants |
| Absorbents | Epilating Agents | Reducing Agents |
| Adhesives | Exfoliants | Skin Bleaching Agents |
| Anticaries Agents | External Analgesics | Skin Protectants |
| Antidandruff Agents | Eyelash Conditioning Agents | Skin-Conditioning Agents |
| Antifoaming Agents | Film Formers | Skin-Conditioning Agents - Emollient |
| Antifungal Agents | Flavoring Agents | Slip Modifiers |
| Antimicrobial Agents | Fragrance Ingredients | Solvents |
| Antioxidants | Hair Conditioning Agents | Sunscreen Agents |
| Binders | Hair Fixatives | Surface Modifiers |
| Buffering Agents | Hair-Waving/Straightening Agents | Surfactants |
| Bulking Agents | Humectants | Surfactants - Cleansing Agents |
| Chelating Agents | Light Stabilizers | Surfactants - Dispersing Agents |
| Colorants | Lytic Agents | Surfactants - Emulsifying Agents |
| Corrosion Inhibitors | Nail Conditioning Agents | Surfactants - Foam Boosters |
| Cosmetic Astringents | Opacifying Agents | Surfactants - Hydrotropes |
| Cosmetic Biocides | Oral Care Agent | Surfactants - Solubilizing Agents |
| Denaturants | Oxidizing Agents | Viscosity Decreasing Agents |
| Depilating Agents | Pesticides | Viscosity Increasing Agents |
| Dispersing Agents - Nonsurfactant | Plasticizers | Viscosity Increasing Agents - Aqueous |
| Astringents | Preservatives | Viscosity Increasing Agents - Nonaqueous |
| | | pH Adjusters |

FIG. 7

| Chemical Classifications | |
|---|---|
| Alcohols | Carboxylic Acids |
| Aldehydes | Color Additives |
| Alkanolamides | Color Additives Lakes |
| Alkanolamines | Complex Lipids |
| Alkoxylated Alcohols | Elements |
| Alkoxylated Amides | Enzymes |
| Alkoxylated Amines | Essential Oils and Waters |
| Alkoxylated Carboxylic Acids | Esters other |
| Alkyl Aryl Sulfonates | Ethers |
| Alkyl Ether Sulfates | Fats and Oils |
| Alkyl Sulfates | Fatty Acids |
| Alkyl-Substituted Amino Acids | Fatty Alcohols |
| Alkylamido Alkylamines | Flavonoids |
| Amides | Fungi, Bacteria and Derivatives |
| Amine Oxides | Glyceryl Esters and Derivatives |
| Amines | Gums and Hydrophilic Colloids |
| Amino Acids | Halogen Compounds |
| Benzophenones | Heterocyclic Compounds |
| Betaines | Hydrocarbons |
| Biological Polymers | Imidazoline Compounds |
| Biological Products | Inorganic Acids |
| Biotechnological Products | Inorganic Bases |
| Botanical Products | Inorganic Salts |
| Carbohydrates excluding gums | Organometallics |
| | Oximes |
| | PABAs |
| | Peptides |
| | Peroxides |
| | Phenols |
| | Phosphorus Compounds |
| | Polymeric Ethers |
| | Polyols |
| | Proteins |
| | Quats |
| | Sarcosinates |
| | Siloxanes and Silanes |
| | Soaps |
| | Sorbitans |
| | Sterols |
| | Sulfonic Acids |
| | Sulfosuccinates |
| | Sulfuric Acid Esters |
| | Synthetic Polymers |
| | Thio Compounds |
| | Tissue Cultures |
| | Transesters |
| | Unsaponifiables |
| | Water |
| | Waxes |

FIG. 8

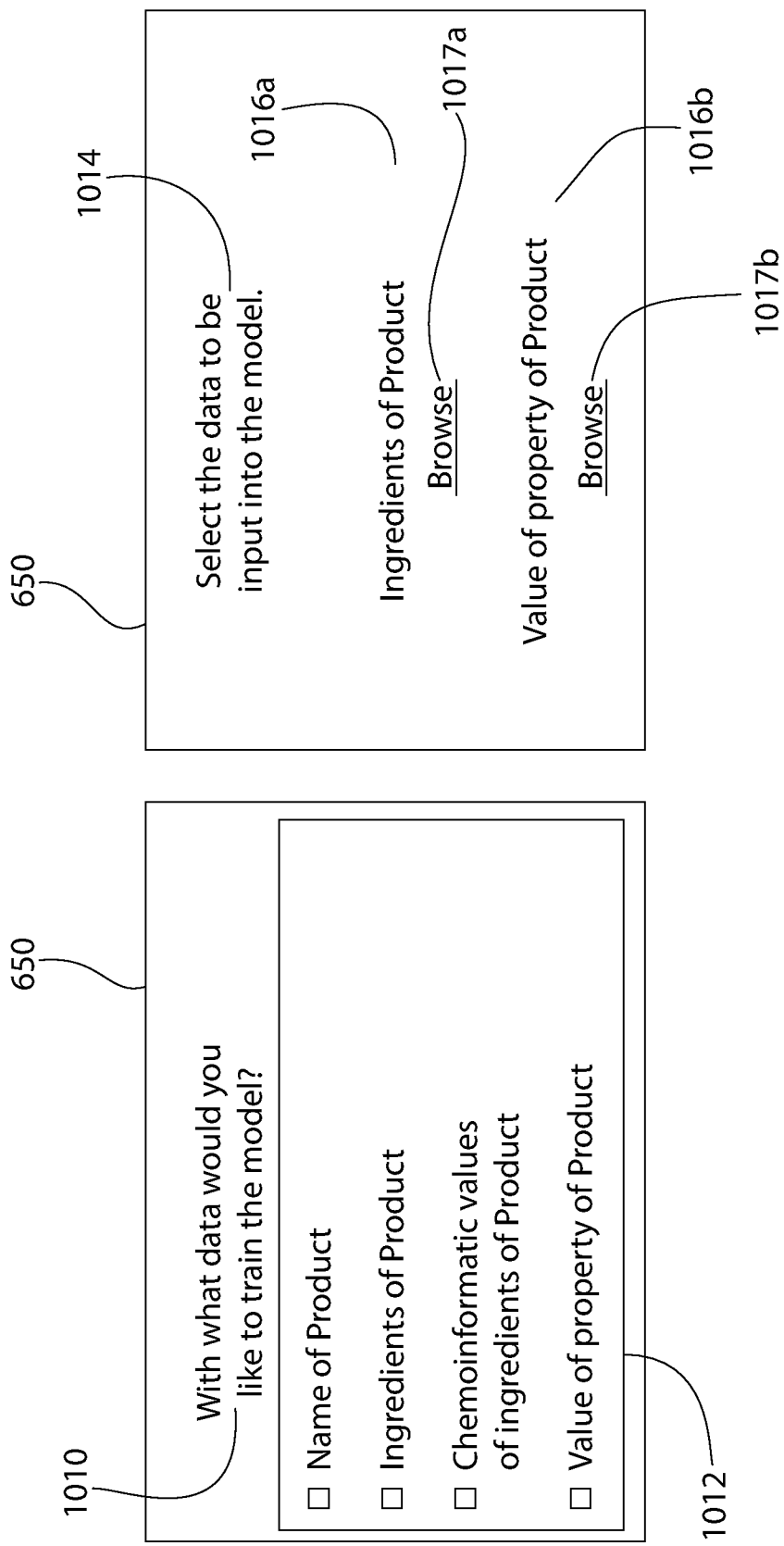

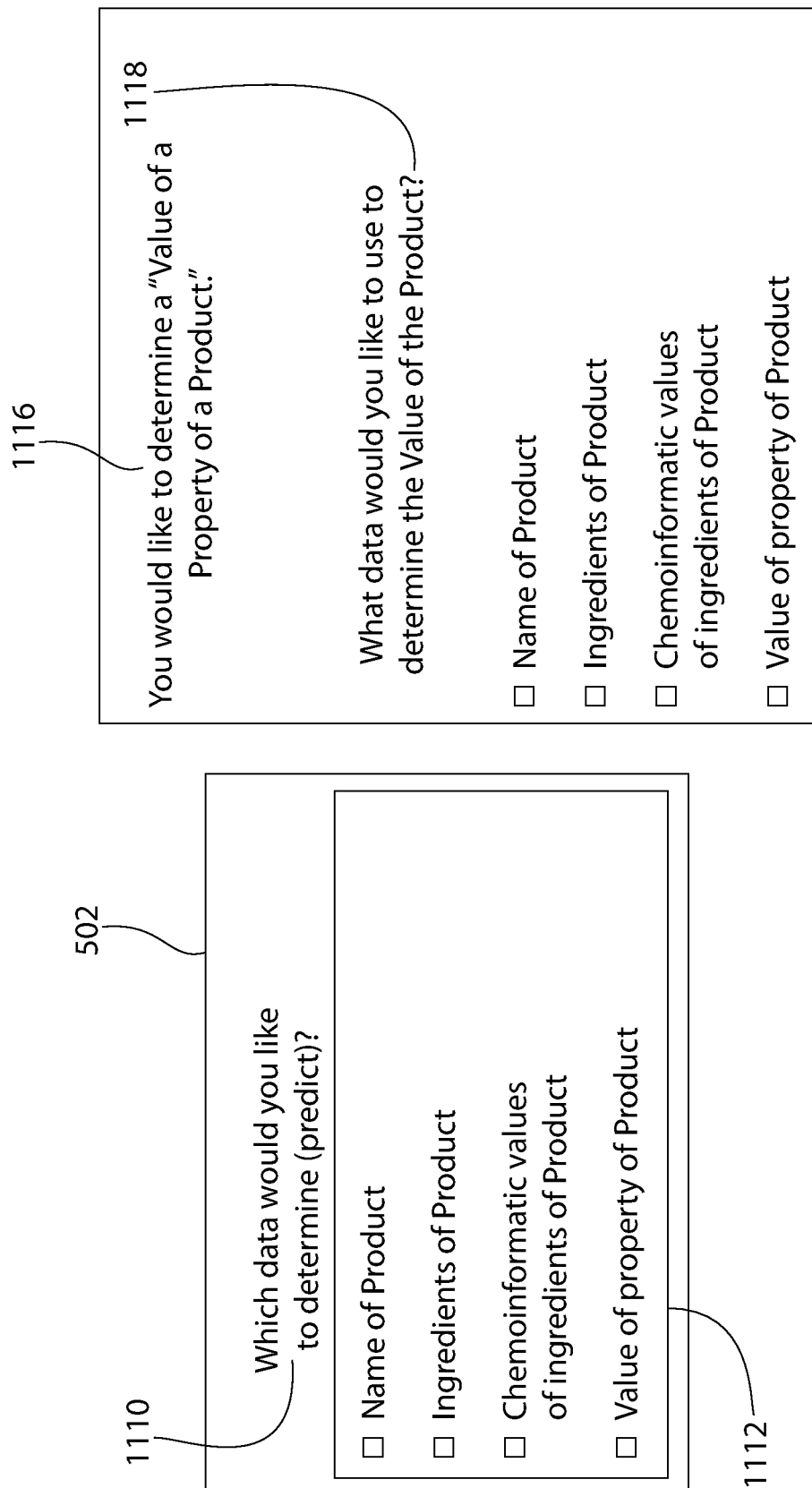

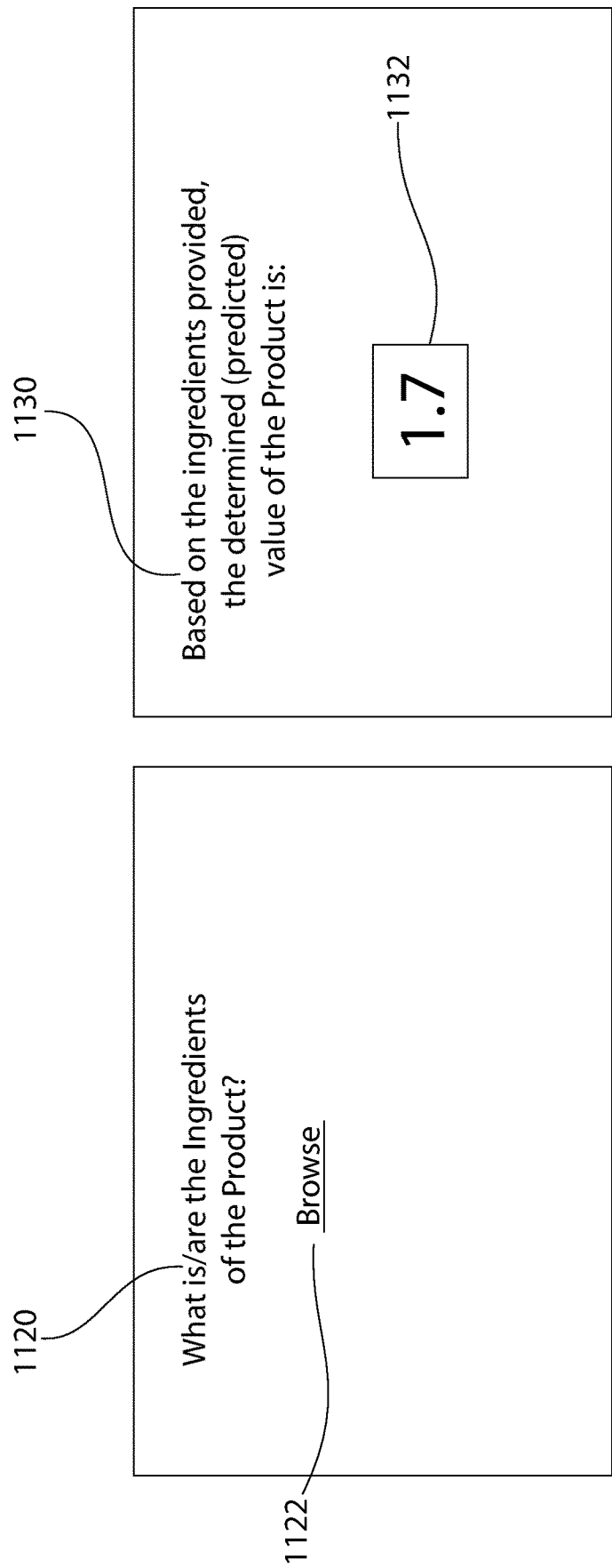

SYSTEMS AND METHODS FOR PRODUCING PERSONAL CARE PRODUCTS

CROSS-REFERENCE TO RELATED PATENT APPLICATION

The present application is a continuation of U.S. patent application Ser. No. 16/731,533, filed Dec. 31, 2019, which are continuation applications of U.S. patent application Ser. No. 16/672,922, filed Nov. 4, 2019, which is a continuation of U.S. patent application Ser. No. 16/452,214, filed Jun. 25, 2019, now granted as U.S. Pat. No. 10,515,715, the contents of which are all hereby incorporated herein by reference in their entireties.

BACKGROUND

Many products are formed of chemical compositions. Chemical compositions typically include many different ingredients. Each of the ingredients have a particular value, such as a chemoinformatic value, associated with the ingredient. Further, one or more properties (e.g., a pH, a consumer perception) of the chemical composition may have unique values, for example, based on the ingredients within the composition. The value of the property of the chemical composition may change due to the interaction of the ingredients within the composition.

Conventional methods exist for predicting values of one or more properties of a chemical composition. However, such methods are often time consuming and nontrivial. For example, conventional approaches to predicting a value of a pH of a chemical composition include (1) experimentally measuring the chemical composition to determine the pH value; and (2) performing a mathematical prediction calculation to determine the pH value (e.g., using known acidity constants, such as pKa values). These approaches, however, are deficient due to the time and/or complexity involved in the respective approaches. Thus, a system and/or method is desired that can determine a value of a property of a chemical composition in a way that requires less time and/or less complexity.

BRIEF SUMMARY

A system, apparatus, and/or method is disclosed for producing a personal care product. An identity of a considered chemical composition may be input into a model (e.g., a machine learning model). The identity of the considered chemical composition may include ingredients. Each of the ingredients of the considered chemical composition may be associated with a value of a chemoinformatic property of chemoinformatic properties of the considered chemical composition. A value of the property of the considered chemical composition may be determined via the model. The value may be based on the identity of the considered chemical composition. The property of the considered chemical composition may be affected by an interaction of at least two of the ingredients of the considered chemical composition. A personal care product comprised of the considered chemical composition may be produced.

A system, apparatus, and/or method is disclosed for producing a personal care product. At least one of an identity of a considered chemical composition or values of chemoinformatic properties of ingredients of the considered chemical composition may be input into a machine learning model. The identity of the considered chemical composition may include ingredients. Each of the ingredients may be associated with a value of a chemoinformatic property of chemoinformatic properties of the considered chemical composition. A fitting parameter value of the considered chemical composition may be determined, via the machine learning model, based on at least one of an identity of the considered chemical composition or values of chemoinformatic properties of ingredients of the considered chemical composition. The fitting parameter value may be associated with a value of a property of a considered chemical composition. The property of the considered chemical composition may be affected by an interaction of at least two of the ingredients of the considered chemical composition. A personal care product comprised of the considered chemical composition may be produced.

A system, apparatus, and/or method is disclosed for producing a personal care product. At least one of values of chemoinformatic properties of ingredients of the considered chemical composition or a value of a property of the considered chemical composition may be input into a model. The property of the considered chemical composition may be affected by an interaction of at least two of the ingredients of the considered chemical composition. The identity of the considered chemical composition may be determined, via the model, based on the at least one of the values of the chemoinformatic properties of the ingredients of the considered chemical composition or the value of the property of the considered chemical composition. A personal care product comprised of the identified considered chemical composition may be produced.

In another aspect, a system, apparatus, and/or method is disclosed for producing a personal care product. Values of chemoinformatic properties of ingredients of a sample chemical composition are received. A value of a property of the sample chemical composition is received in which the property is affected by an interaction of at least two of the ingredients. The values of the chemoinformatic properties of the ingredients of the sample chemical composition and the value of the property of the sample chemical composition are input into a model. An identity of the considered chemical composition is determined, via the model, based on at least one of (1) values of chemoinformatic properties of ingredients of the considered chemical composition or (2) a value of a property of the considered chemical composition. The personal care product comprised of the considered chemical composition is produced.

In another aspect, a system, apparatus, and/or method is disclosed for determining a value of a property of a considered chemical composition. An identity of a sample chemical composition may be received. A sample chemical composition may comprise ingredients. Each of the ingredients may be associated with a value of a chemoinformatic property of chemoinformatic properties of the sample chemical composition. A value of a property of the sample chemical composition may be received. The property of the sample chemical composition may be affected by an interaction of at least two of the ingredients of the sample chemical composition. The value of the property of the sample chemical composition and at least one of (1) the identity of the sample chemical composition or (2) the values of the chemoinformatic properties of the ingredients of the sample chemical composition may be input into a model. The value of the property of the considered chemical composition may be determined, via the model, based on at least one of (1) an identity of the considered chemical composition or (2) values of chemoinformatic properties of ingredients of the considered chemical composition. The property of the considered chemical composition may be affected by an interaction of at least two of the ingredients of the considered chemical composition.

In another aspect, a value of a property of a considered chemical composition may be determined. An identity of a sample chemical composition may be received. The identify may include ingredients. One or more (e.g., each) of the ingredients may be associated with a value of a chemoinformatic property of chemoinformatic properties of the sample chemical composition. A value of a sample physiochemical property of the sample chemical composition may be received. The sample physiochemical property of the sample chemical composition may be affected by an interaction of at least two of the ingredients of the sample chemical composition. The value of the sample physiochemical property of the sample chemical composition may be input into a model. The identity of the sample chemical composition and/or the values of the chemoinformatic properties of the ingredients of the sample chemical composition may be input into a model. The value of a considered physiochemical property of the considered chemical composition may be determined via the model. The value may be based on an identity of the considered chemical composition and/or values of chemoinformatic properties of ingredients of the considered chemical composition. The considered physiochemical property of the considered chemical composition may be affected by an interaction of at least two of the ingredients of the considered chemical composition. The considered physiochemical property may be different than the sample physiochemical property.

In another aspect, a value of a property of a considered chemical composition may be determined. An identity of a characteristic of interest may be received. Identities of sample chemical compositions may be received. Each of the sample chemical compositions may comprise ingredients each being associated with a value of a chemoinformatic property of chemoinformatic properties of the sample chemical composition. For each of the sample chemical compositions, a value of a property that is affected by an interaction of at least two of the ingredients of the sample chemical composition may be received. For each (e.g., only each) of the sample chemical compositions having the characteristic of interest, the value of the property of the sample chemical composition and at least one of (1) the identity of the sample chemical composition or (2) the values of the chemoinformatic properties of the ingredients of the sample chemical composition may be input into a model. The value of the property of the considered chemical composition may be determined via the model. The value may be based on at least one of (1) an identity of the considered chemical composition or (2) values of chemoinformatic properties of the ingredients of the considered chemical composition. The property of the considered chemical composition may be affected by an interaction of at least two ingredients of the considered chemical composition.

In another aspect, a product comprised of a considered chemical composition having a value of a considered chemical property may be produced. An identity of a sample chemical composition comprising ingredients may be received. Each of the ingredients may be associated with a value of a chemoinformatic property of chemoinformatic properties of the sample chemical composition. A value of a training chemical property of the sample chemical composition may be received. The value of the training chemical property may be based on at least one of an experimental measurement of the value of the training chemical property or a mathematical measurement of the value of the training chemical property. A learning model may be constructed using values of the chemoinformatic properties of the sample chemical composition and the value of the training chemical property of the sample chemical composition. The value of the considered chemical property may be input into the learning model. Values of chemoinformatic properties of the considered chemical composition having the value of the considered chemical property may be determined via the learning model and/or based on the value of the considered chemical property. The product comprising the considered chemical composition having the value of the considered chemical property may be produced.

In another aspect, a value of a considered chemical composition having ingredients may be determined. An identity of a sample chemical composition having a defined value of a chemical property may be received. The sample chemical composition may be comprised of ingredients that may be different than ingredients of the considered chemical composition. A training set comprising the identity of the sample chemical composition and the defined value of the chemical property of the sample chemical composition may be generated. A model for determining a value of a chemical property of the considered chemical composition may be constructed based on the training set. The value of the chemical property of the considered chemical composition may be determined via the model, for example, based on an identity of the considered chemical composition and the training set. The value of the chemical property of the considered chemical composition may be received.

In another aspect, an identity of a sample chemical composition comprising ingredients may be received. Each of the ingredients may be associated with a value of a chemoinformatic property of chemoinformatic properties of the sample chemical composition. A value of a fitting parameter associated with a value of a property of the sample chemical composition may be received. The property of the sample chemical composition may be affected by an interaction of at least two of the ingredients of the sample chemical composition. The fitting parameter value associated with the value of the property of the sample chemical composition and/or at least one of (1) the identity of the sample chemical composition or (2) the values of the chemoinformatic properties of the ingredients of the sample chemical composition may be input into a model. A fitting parameter value of the considered chemical composition may be determined via the model. The fitting parameter value may be based on at least one of (1) an identity of the considered chemical composition or (2) values of chemoinformatic properties of ingredients of the considered chemical composition.

In another aspect, a considered chemical composition may be identified. Values of chemoinformatic properties of ingredients of a sample chemical composition may be received. A value of a property of the sample chemical composition may be received. The property may be affected by an interaction of at least two of the ingredients. The values of the chemoinformatic properties of the ingredients of the sample chemical composition and the value of the property of the sample chemical composition may be input into a model. An identity of the considered chemical composition may be determined via the model, for example, based on at least one of (1) values of chemoinformatic properties of ingredients of the considered chemical composition or (2) a value of a property of the considered chemical composition. The property of the considered chemical composition may be affected by an interaction of at least two of the ingredients of the considered chemical composition.

In another aspect, identities of components of a first composition may be received. Each of the components may have a value of a predefined characteristic of predefined characteristics. A value of a property of the first composition may be received. The property may be affected by an interaction of at least two of the components of the first composition. A learning model may be trained using the values of the predefined characteristics of the components of the first composition and the value of the property of the first composition. Identities of second components of a second composition may be provided to the learning model. At least one of the second components may be different than at least one of the first components. A value of a property of the second composition may be determined via the learning model. The property of the second composition may be affected by an interaction of at least two of the components of the second composition.

In another aspect, a value of a property of a considered chemical composition may be determined. An identity of the considered chemical composition from chemical compositions associated with a personal care product may be received. The considered chemical composition may include ingredients. Values of chemoinformatic properties may be received. Each value may be associated with a respective one of the ingredients of the considered chemical composition. The value of the property of the considered chemical composition may be determined based on at least one of (1) the identity of the considered chemical composition or (2) the values of the chemoinformatic properties associated with the respective one of the ingredients of the considered chemical composition. The model may be trained by at least one of (1) an identity of a chemical composition or (2) values of chemoinformatic properties of ingredients of the chemical composition with a value of a property of the chemical composition. The value of the property of the considered chemical composition may be affected by an interaction of at least two of the ingredients of the considered chemical composition.

In another aspect, a model may be created to determine a value of a property of a considered chemical composition. An identity of a sample chemical composition comprising ingredients may be received. Each of the ingredients may be associated with a value of a chemoinformatic property of chemoinformatic properties of the sample chemical composition. A value of a property of the sample composition may be received. The property may be affected by an interaction of at least two of the ingredients of the sample chemical composition. A model may be trained to determine the value of the property of the considered chemical composition by processing the value of the property of the sample chemical composition and at least one of (1) an identity of the sample composition or (2) the values of the chemoinformatic properties of the ingredients of the sample chemical composition. The model may be configured to determine the value of the property of the considered chemical composition based on at least one of (1) an identity of the considered chemical composition or (2) values of chemoinformatic properties of ingredients of the considered chemical composition.

BRIEF DESCRIPTION OF THE DRAWINGS

The present invention will become more fully understood from the detailed description and the accompanying drawings, wherein:

FIG. 1A is a table of ingredients of an exemplary composition;

FIG. 1B is a table of example properties of composition in which consumers may have a perception;

FIG. 2B is a table of ingredients of another exemplary composition, providing identities of the ingredients and percentages of the ingredients;

FIG. 7 is a table of example functions of ingredients of a composition;

FIG. 8 is a table of example classifications of ingredients of an exemplary composition;

FIGS. 10A, 10B, 10C are example graphical user interfaces (GUIs) for training a property engine;

FIGS. 11A, 11B, 11C, 11D are example graphical user interfaces (GUIs) for receiving a determined value via a property engine.

DETAILED DESCRIPTION

Figure 2A:
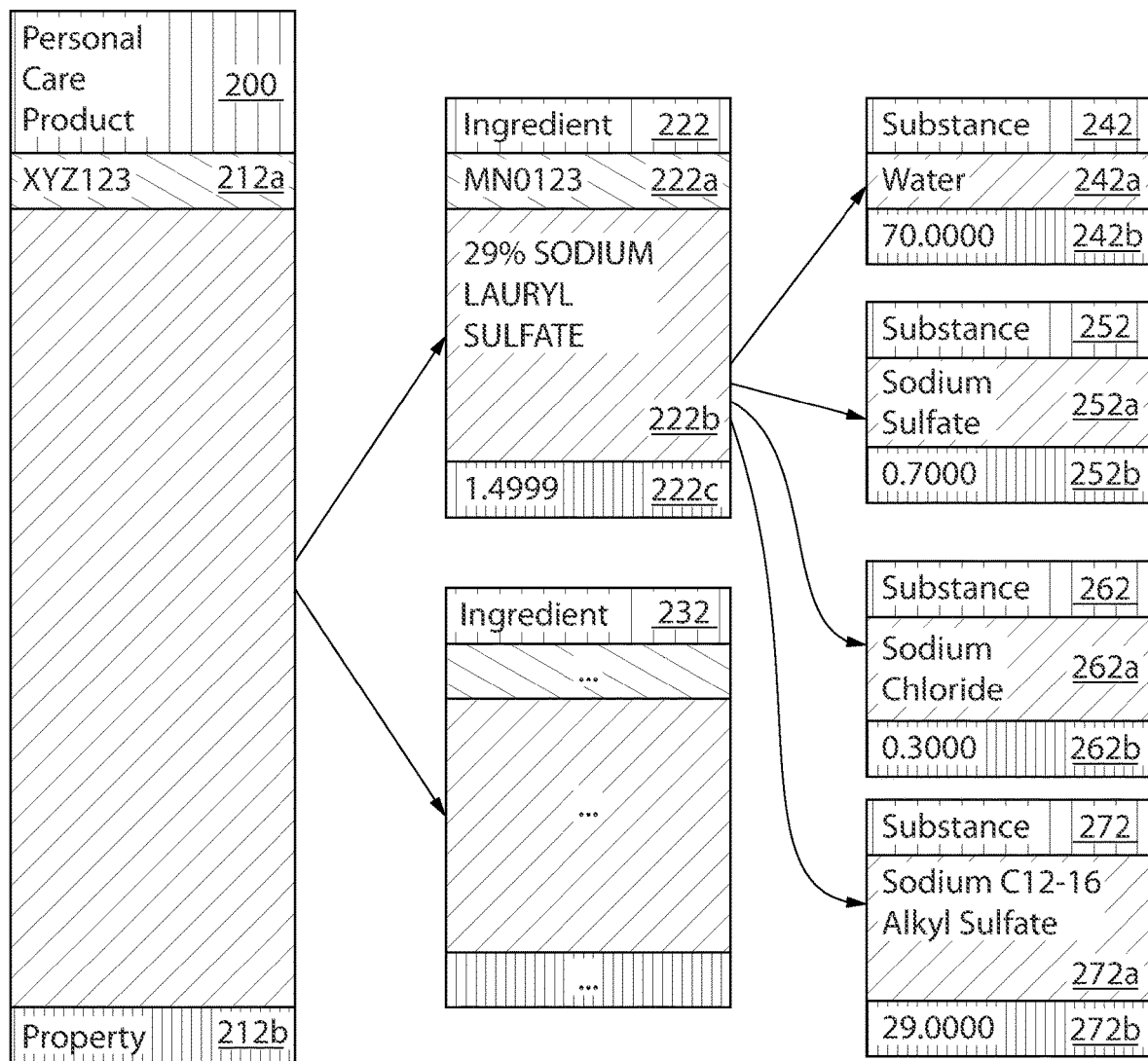
FIG. 2A is a block diagram of example components of a composition, the components including ingredients and substances of the composition.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present invention. The discussion herein describes and illustrates some possible non-limiting combinations of features that may exist alone or in other combinations of features. Furthermore, as used herein, the term "or" is to be interpreted as a logical operator that results in true whenever one or more of its operands are true. Furthermore, as used herein, the phrase "based on" is to be interpreted as meaning "based at least in part on," and therefore is not limited to an interpretation of "based entirely on."

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Features of the present invention may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Compositions may include one or more ingredients. For example, a composition may include a first, second, third, etc. ingredient. One or more of the ingredients of a composition may have an effect on one or more other ingredients of the composition. Also, or alternatively, one or more of the ingredients may have an effect on the composition (e.g., the composition as a whole).

A composition may be a chemical composition. The chemical composition may form a product. The chemical composition (e.g., product formed from the chemical composition) may be used for one or more purposes. For example, a product formed from a chemical composition may be used for cooking; cleaning; personal care; treating/testing for diseases, disorders, conditions; as well as one or more other purposes. A composition (e.g., chemical composition) may be used for performing tasks. For example, a chemical composition may be used for performing tests, such as water purity tests.

A chemical composition may form a personal care product, although a personal care product is for illustration purposes only and a chemical composition may form one or more other products. A personal care product may exist for enhancing a user's health, hygiene, appearance, etc. Such personal care products may comprise one or more chemical compositions that are comprised of one or more ingredients. Personal care products may include oral care products comprising oral care compositions, skin care products comprising skin care compositions, hair care products comprising hair care compositions, as well as other products and/or chemical compositions.

Oral care composition, as used herein, may include a composition for which the intended use can include oral care, oral hygiene, oral appearance, or for which the intended use may comprise administration to the oral cavity. Skin care composition, as used herein, may include a composition for which the intended use may include promotion or improvement of health, cleanliness, odor, appearance, and/or attractiveness of skin. Hair care compositions, as used herein, may include a composition for which the intended use may include promotion or improvement of health, cleanliness, appearance, and/or attractiveness of hair. The compositions may be used for a wide variety of purposes, including for enhancing personal health, hygiene, and appearance, as well as for preventing or treating a variety of diseases and other conditions in humans and in animals.

FIG. 1A shows a table of data associated with an example composition. The composition may be a chemical composition, such as chemical composition 100. Chemical composition 100 may form a product, such as a personal care product. As can be seen from FIG. 1A, chemical composition 100 may include several ingredients. For example, chemical composition 100 may include glycerin, sodium lauryl sulfate, zinc citrate, as well as one or more other ingredients. Each of the ingredients of the chemical composition 100 (e.g., the chemical composition forming a personal care product) may be included in the personal care product to provide one or more predefined features. As provided in FIG. 1A, features of the ingredients may include providing sweetness to the chemical composition 100, providing stabilizing factors to the chemical composition 100, etc. For example, sodium lauryl sulfate is an ingredient of the chemical composition 100 that may be used as a solubilizing or cleansing agent for the chemical composition 100.

FIG. 1B shows a table of additional data associated with an example composition, such as chemical composition 100. In an example the chemical composition may form a product, such as a personal care product. The data provided in FIG. 1B may relate to a consumer perception of a personal care product. As can be seen from FIG. 1B, a consumer may perceive a chemical composition according to several categories and/or features. For example, consumers may have perceptions about the color, stickiness, wetness, ease of use, sweetness, etc., of a chemical composition. A consumer may have a preference for a personal care product based on the perception of one or more features of the chemical composition forming the personal care product. For example, a consumer may prefer that a toothpaste have a certain color, that a shampoo have a certain smell, that a deodorant have a certain dispersibility, etc. One or more consumers may rate a personal care product based on one or more perception values that the consumer has regarding the personal care product. The values of consumer perceptions may be obtained in a variety of ways, including a survey (e.g., a paper or online survey), a clinical trial, commercial success of the personal care product, etc.

Consumer perceptions of a chemical composition (e.g., a chemical composition forming a personal care product) may be based on one or more of the ingredients of the personal care product. Said another way, a consumer perception value may be affected by one or more ingredients of the personal care product. For example, a particular ingredient may cause a personal care product to be more white or less white, to be more sticky or less sticky, to cause more of a burning sensation or less of a burning sensation, etc.

FIG. 2A shows a depiction of data associated with a composition (e.g., a chemical composition). The composition may form a product, such as a personal care product 200. For example, data associated with personal care product 200 may include an identity, such as a name of the personal care product, ingredients of the personal care product, chemoinformatic values of ingredients of personal care product, or another identifier used to identify the personal care product. For example, personal care product 200 may be associated with a unique number 212a that may be referenced by a user and/or computer when referring to the personal care product. Each personal care product 200 may have one or more other values and/or properties, such as property 212b. Property 212b may be a chemical property associated with the chemical composition of the personal care product. For example, property 212b may be a physiochemical property of the chemical composition of the personal care product. The physiochemical property of the chemical composition may relate to a physical property or a chemical property of the chemical composition of the personal care product. For example, property 212b may be a pH value of the personal care product. The value of property 212b may be affected by one or more ingredients of the personal care product.

Property 212b may be a consumer perception of the personal care product, such as the perceptions shown in FIG. 1B. For example, consumers may have perceptions about the color, stickiness, wetness, ease of use, sweetness, etc., of the personal care product. The consumer perceptions of the personal care product may be based on one or more of the ingredients of the personal care product. For example, an ingredient may cause a personal care product to be more white or less white, to be more sticky or less sticky, to cause more of a burning sensation or less of a burning sensation, etc.

As described herein, a chemical composition may form a personal care product. The chemical composition may be comprised of one or more ingredients (e.g., ingredient data), such as ingredients 222, 232. Each ingredient may include an identity, such as a name of the ingredient or other identifier used to identify the ingredient. For example, ingredient 222 may include a name 222b and/or an identifier 222a. Ingredient 222 may include other information, such as the percentage of the personal care product that comprises the ingredient. For example, as shown in 222c, ingredient 222 (e.g., sodium lauryl sulfate) may be 1.4999% of the personal care product 200. Ingredient data may include one or more other properties and/or values of the properties.

Each ingredient may further be made up of one or more substances. As shown in FIG. 2A, ingredient 222 may be comprised of four substances: water 242, sodium sulfate 252, sodium chloride 262, and sodium C12-16 Alkyl Sulfate 272. Data may be associated with one or more (e.g., each) of the substances. For example, each substance may include an identity, such as a name 242a, 252a, 262a, 272a of the substance or other identifier used to identify the substance. As an example, substance 242 may have a name 242a of water. The substance (such as substance 242, 252, 262, 272) may include one or more other values, such as the percentage 242b that the substance makes up of the ingredient, chemoinformatic properties of the ingredients (e.g., substances of the ingredients), etc. For example, substance 242 (i.e., water) may comprise 70% of the ingredient 222 sodium lauryl sulfate, as shown on 242b. Substance 272 may include chemoinformatic properties such as a chemical class, an HLB value, a surface area (e.g., topological polar surface area), etc. As shown on FIG. 2A, example information may include a chemical class of Alkyl Sulfate, an HLB value of 40, and/or a topological polar surface area of 74.8 squared Angstroms. In other examples, however, one or more substances may have one or more (e.g., different) chemoinformatic properties having one or more different values.

As described herein, property 212b of personal care product may be affected by interactions of one or more of the ingredients of the chemical composition that is the personal care product 200. Examples of property 212b may relate to a pH, fluoride (e.g., fluoride stability), viscosity (e.g., viscosity stability), viscoelasticity, abrasion (e.g., stain removal and dentin abrasion), color, turbidity, analyte concentration, specific gravity, consumer perception (e.g., sweetness, stickiness, fragrance), etc., of a personal care product.

The value of property 212b of the chemical composition of the personal care product may be determined by experimentally measuring the value of the property. By experimentally measuring the property of the personal care product, the actual value of the property may be determined. The value of the property 212b may be determined via a mathematical (e.g., thermodynamic) calculation of the value of the property. For example, a database of personal care product compositions may be compiled. The compositions may include one or more compositions. A catalogue (e.g., a hand-evaluated catalogue) may contain one or more constants (e.g., metal binding constants, surface acidity constant, etc.), and/or one or more solubility products, for example. Speciation calculations may be performed on personal care product compositions. The speciation calculations may be used to determine the activity of one or more (e.g., each) ion of a personal care product composition. The negative log of the hydrogen ion may correspond (e.g., activity correspond) to a calculated value (e.g., the calculated pH value) of the personal care product composition.

The value of the property 212b may be determined by receiving consumer perceptions of one or more attributes of the personal care product. For example, clinical consumer trials may be used to determine consumer perceptions about the personal care product. The clinical consumer trials may determine how consumers (e.g., potential consumers) perceive the personal care product. For example, clinical consumer trials may determine how consumers feel about the color (e.g., whiteness), stickiness, wetness, sweetness, fragrance, bitterness, ease of use, etc. of the personal care product. Consumer perceptions may be determined via other methods, including surveys (e.g., online and paper surveys), commercial success, etc. FIG. 1B provides a list of example properties of personal care product in which consumers may have a perception.

FIG. 2B is an example table of data relating to a composition. The composition may be chemical composition that may form a personal care product. As described herein, examples of personal care products may include oral care products (e.g., a toothpaste, mouthwash, etc.), hair products (e.g., a shampoo, hair gel, etc.), skin products (e.g., moisturizers, soaps, etc.), etc. A personal care product may include ingredients, such as the example ingredients named under column 282. For example, the chemical composition forming the personal care product may include ingredients such as sorbitol, water, glycol, etc.

The ingredients (e.g., each of the ingredients) may be identified in one or more ways. For example, the ingredients may be identified by name. Also, or alternatively, the ingredients may be identified by an identification number (e.g., a unique identification number), such as by the identification numbers provided under column 280. The identification number may be used by a user and/or one or more software applications to identify the ingredient. The identification number may be used to conceal the true identity of the ingredients, for example, in instances when the identification of the ingredients is confidential. The identification numbers may be randomly generated, may be generated and/or listed in an order (such as an increasing or decreasing order), etc. Although the table of FIG. 2B shows the identifications under column 280 as alphanumeric characters, it will be understood by those of skill in the art that the identifications may be represented as any combination of numbers, letters, special characters, etc.

FIG. 2B further provides values, such as the percentage values shown in column 284. The percentage values may relate to the weight percentage of the ingredient in the composition (e.g., a personal care product). For example, as shown in FIG. 2B, water may comprise 10 to 30 percent of the composition, and sodium saccharin may comprise 0.1 to 1 percent of the total weight of the composition.

As described herein, personal care products may be formed of (e.g., formulated using) one or more chemical compositions comprising one or more ingredients. Formulating personal care products using more than one chemical composition and/or one or more ingredients may present a number of challenges. For example, combining chemical compositions may cause values of properties of the chemical composition forming the personal care product to change. As an example, combining two or more ingredients in a chemical composition may cause the pH value to change. The pH value may be changed in an unpredictable way, for example, based on the interaction of the two or more ingredients.

As adding, removing, and/or mixing ingredients within a chemical composition may affect values of properties of the chemical composition, it may be difficult to create personal care products in which the addition, reduction, or mixing of ingredients is required. For example, personal care products may be required to be pharmaceutically and/or cosmetically acceptable for their intended uses and/or purposes. The intended uses and/or purposes may be based on a value of a property (e.g., pH) of the chemical composition. By combining new ingredients to a chemical composition, or removing ingredients from a chemical composition, a value of the property (e.g., a value of pH) of the chemical composition may change such that the chemical composition forming the personal care product is no longer suitable for the personal care products intended purposes.

Chemical compositions forming personal care products may contain therapeutic active materials that may (e.g., may only) deliver desired results if the compositions have not exhibited a chemical degradation. By combining new ingredients to a chemical composition, or removing ingredients from a chemical composition, a value of the property of the chemical composition may change such that the chemical composition forming the personal care product incurs a chemical degradation. Such a chemical degradation may cause the personal care product to no longer be suitable for consumer use.

Chemical compositions forming personal care products may contain cosmetically functional materials that may (e.g., may only) deliver the material to the oral cavity, skin, and/or hair, etc. at effective levels under the conditions that they are typically used by the consumer. By combining new ingredients to a chemical composition, or removing ingredients from a chemical composition, a value of the property of the chemical composition may change such that the chemical composition forming the personal care product no longer performs at the required effective levels.

Chemical compositions forming personal care products may (e.g., may only) exhibit an aesthetic appearance for a time period. Such aesthetic appeal of chemical compositions may be important, for example, as such aesthetic appeal may have significant effects on consumer acceptance and usage. By combining new ingredients to a chemical composition, or removing ingredients from a chemical composition, a value of the property of the chemical composition may change such that the chemical composition forming the personal care product is no longer aesthetically pleasing.

Chemical compositions forming personal care products may exhibit one or more attributes that are perceived by a consumer. For example, chemical compositions forming a personal care product may exhibit a flavor, sweetness, ease of use, etc., as perceived by a consumer. By combining new ingredients to a chemical composition, or removing ingredients from a chemical composition, a value of the property of the chemical composition may change such that the chemical composition forming the personal care product affects the consumer perception of the personal care product. For example, the value of the property of the chemical composition may be affected such that the personal care product exhibits a more minty flavor, a more salty taste, etc.

As described herein, it may be possible to determine a value of a property of a chemical composition forming a personal care product. For example, a value of a property of a personal care product composition may be experimentally measured, mathematically calculated, and/or received via clinical consumer trials. However, such techniques may be time consuming, nontrivial, and/or impossible, as the personal care product composition may include dozens (or more) of ingredients. Machine learning techniques may be used to determine one or more values of properties of a chemical composition.

Figure 3A:
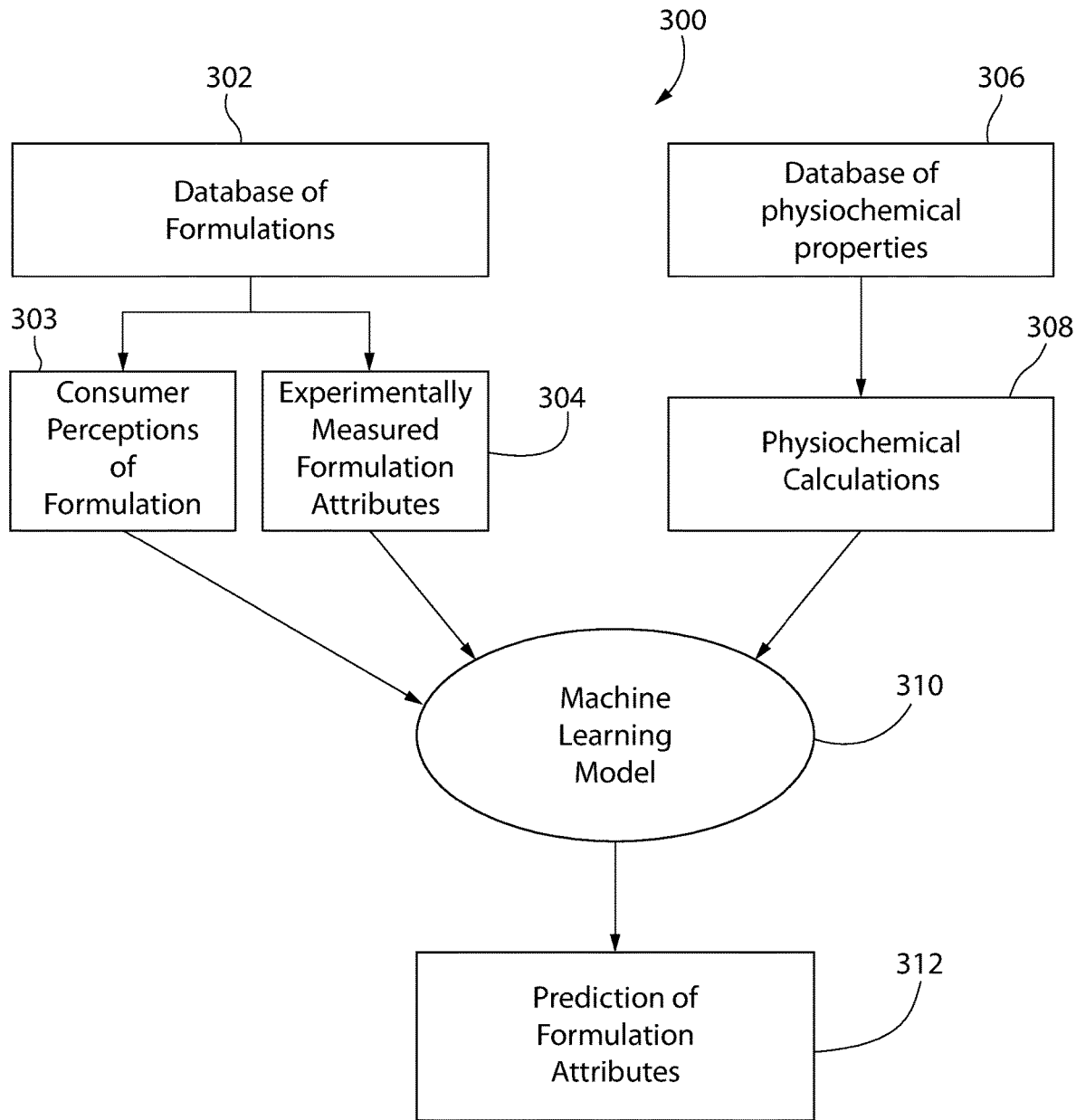
FIG. 3A is an example process for determining a value of a composition using machine learning rules.

FIG. 3A shows an example process 300 for using machine learning techniques to determine (e.g., predict) an attribute. The attribute may include an identity of a composition, ingredients of a composition, a value of a property of a composition, etc. For example, the attribute may include an identity of a chemical composition forming a personal care product, ingredients of a chemical composition forming a personal care product, a value of a property (e.g., a pH value, a fluoride stability value, a viscosity value, an abrasion value, a specific gravity value, a consumer perception value) of a chemical composition forming a personal care product, etc. Although the disclosure may describe the determination (e.g., prediction) of an identity of a chemical composition forming a product (e.g., personal care product) or a value of a property of the chemical composition forming the product (e.g., personal care product), it should be understood that machine learning techniques may also, or alternatively, be used to determine (e.g., predict) other values, such as other identities of products, values of chemoinformatic properties of ingredients of products, etc.

At 302, one or more identities of chemical compositions (e.g., sample chemical compositions of a personal care product) may be stored, for example, in a database. The identity of the chemical composition may include a name of a chemical composition, ingredients of the chemical composition (e.g., formulations of the chemical composition), etc. For example, as shown in FIG. 2A, the identity of the chemical composition may include chemoinformatic properties (e.g., chemoinformatic values) of each of the ingredients of the chemical composition. The identity of a chemical composition may be received from one or more of the databases.

At 303, one or more perceptions of chemical compositions forming one or more products (e.g., personal care products) may be determined and/or received. The perceptions of the chemical compositions may be determined and/or identified via consumers (e.g., potential consumers). The perceptions may be determined and/or identified via clinical consumer trials, for example. The perceptions may include the whiteness of the personal care product, how minty the personal care product is, the sweetness of the personal care product, etc. The perceptions of the chemical compositions may be affected by one or more ingredients of the chemical composition forming the personal care product. For example, one or more ingredients may affect how minty a consumer perceives the personal care product to be, how sweet the consumer perceives the personal are product to be, how white the consumer perceives the personal are product to be, etc.

At 304, values of properties of chemical compositions forming one or more products (e.g., personal care products) may be determined via experimental measurements. The values of the properties may be affected by one or more ingredients of the chemical composition. The experimentally measured values of properties of the chemical composition may be identified by performing actual measurements of the values of the properties of the chemical compositions. The experimentally measured values of properties of the chemical composition may be identified by retrieving the experimentally measured values of the properties from a database, for example, after the experimentally measured values of the properties have been stored in a database. The experimentally measured values of properties of the chemical composition (e.g., sample chemical compositions) may be received.

At 306, one or more values of a chemical composition forming a personal care product may be determined and/or stored, for example, in a database. The one or more values of the chemical composition may relate to physiochemical properties of a chemical composition. The value of a physiochemical property may include a value for one or more (e.g., each) ingredients of the chemical composition. The value of a physiochemical property may be received, for example, from one or more databases.

At 308, the values of physiochemical properties of the chemical composition may be identified and/or determined. The values of physiochemical properties of the chemical composition may be determined by measuring the physiochemical properties of the ingredients of the chemical composition, calculating (e.g., mathematically calculating) predicted values of the physiochemical properties of the chemical compositions, looking up the values of the physiochemical properties (e.g., via a database, look-up table, etc.), etc. The values of physiochemical properties of the chemical composition may be identified and/or determined via thermodynamic calculations of the physiochemical properties.

At 310, data may be input into a machine learning model, as described herein. For example, identities of chemical compositions may be input into the model. Identities of chemical compositions may include names of one or more of the chemical compositions, identities of ingredients of the chemical compositions, values of chemoinformatic properties (of ingredients) of the chemical compositions, etc. Values of properties of the chemical composition may be input into the machine learning model. For example, values of properties (e.g., experimentally measured values, mathematically calculated values, consumer perceived values) of the chemical composition may be input into the model. Data related to chemical compositions may be input into the model to train the model, in examples. In other examples, data related to chemical compositions may be input into the model to determine values (e.g., other values) of the chemical compositions.

An association may be input into the model. For example, there may be an association between an identity (e.g., ingredients) of a chemical composition and a value of a property of the chemical composition. The ingredients of a chemical composition (e.g., a sample chemical composition) and the associated value of the property of the chemical composition (e.g., a sample chemical composition) may be input into a machine learning model, for example, to train the machine learning model.

At 312, the machine learning model may determine (e.g., predict) a value of one or more pieces of data relating to the chemical composition. For example, if an identity of a chemical composition (e.g., a considered chemical composition) is input into the machine learning model, the machine learning model may determine (e.g., predict) a value of a property of the chemical composition based on the identity of the chemical composition. Conversely, if a value of a property of a chemical composition (e.g., considered chemical composition) is input into the machine learning model, the machine learning model may determine (e.g., predict) an identity of the chemical composition based on the value of the property of the chemical composition.

Figure 3B:
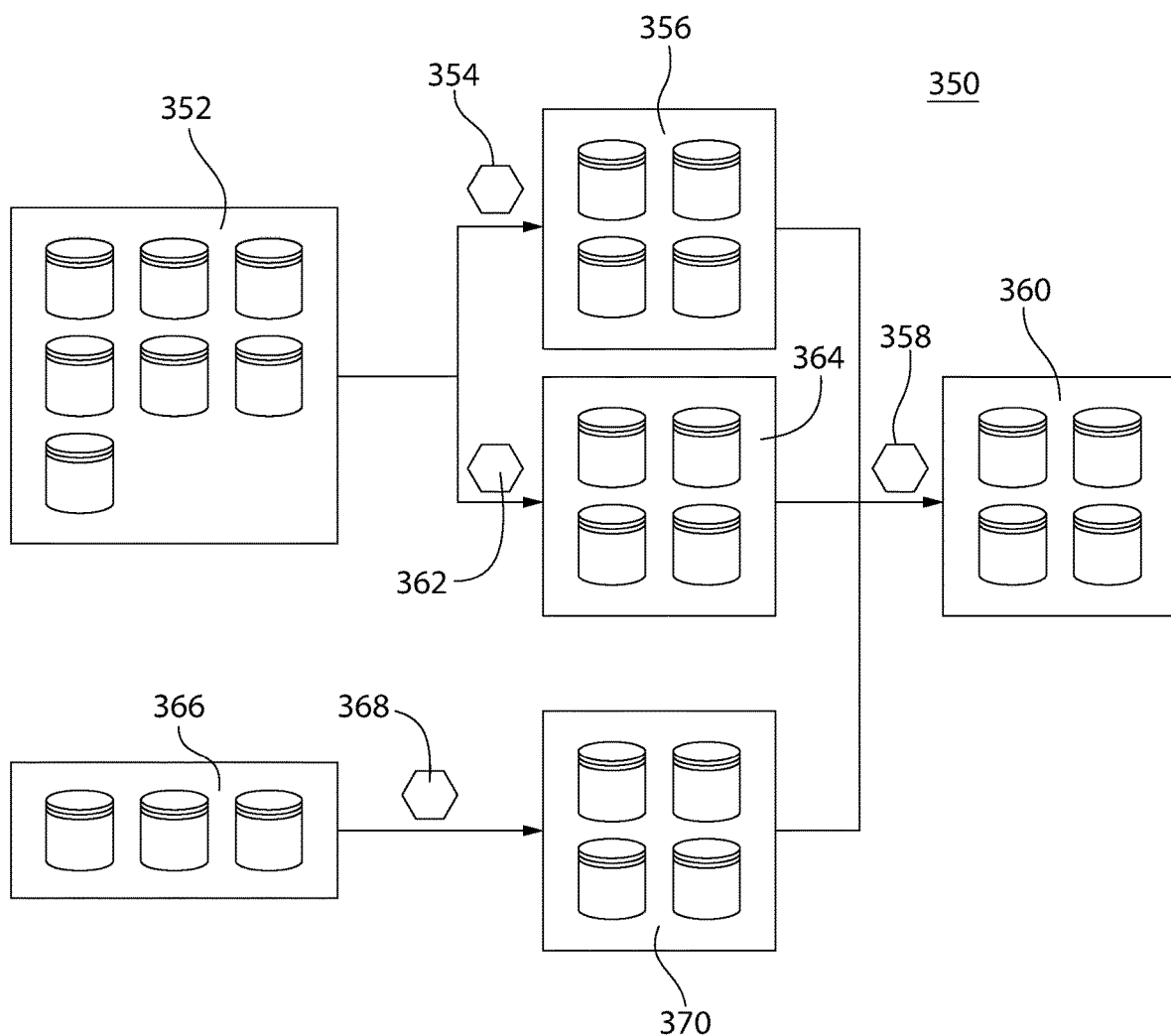
FIG. 3B is an exemplary system for determining a value of a composition.

FIG. 3B is an example diagram of system 350 for determining information relating to a composition, such as a chemical composition forming a product (e.g., a personal care product). The information may relate to an identity of a chemical composition, chemoinformatic values of the chemical composition, as well as one or more other values relating to a product. System 350 may be a data warehouse, in an example. For example, system 350 may include one or more databases for receiving, storing, and/or providing data and/or one or more processors for processing the data received, stored, and/or provided by one or more of the databases.

System 350 may include element 352, which may include one or more databases. For example, element 352 may include one or more databases receiving, storing, and/or providing formulation identifiers, raw materials in one or more (e.g., each) of the formulations, and/or weight percentages of one or more (e.g., each) of the raw materials in a formulation. Element 352 may include one or more databases receiving, storing, and/or providing formulation identifiers, descriptive sales, and/or logistical information. Element 352 may include one or more databases receiving, storing, and/or providing raw material identifiers, cost(s), manufacturer information, and/or logistical information. Element 352 may include one or more databases receiving, storing, and/or providing raw material identifiers, chemicals in one or more (e.g., each) raw material, and/or weight percentages of one or more (e.g., each) chemical in a raw material. Element 352 may include one or more databases receiving, storing, and/or providing raw material identifiers and/or informatic (e.g., chemoinformatic) properties of the raw materials. Element 352 may include one or more databases receiving, storing, and/or providing chemical identifiers and/or informatic (e.g., chemoinformatic) properties of the chemicals. Element 352 may include one or more databases receiving, storing, and/or providing thermodynamic and kinetic reaction constants between chemicals, such as all known thermodynamic and kinetic reaction constants between all chemicals.

At 354, feature selection, representation, and/or engineering may be performed. For example, rules (e.g., algorithms) may perform feature selection, representation, and/or engineering.

System 350 may include element 356, which may include one or more databases. For example, element 356 may include one or more databases receiving, storing, and/or providing formulation identifiers, select features in a (e.g., each) formulation (such as a combination of identifiers, material informatics, chemical informatics, etc.), and/or representation (e.g., quantitative representation) of the abundance of a feature in a formulation.

At 362, chemical speciation calculations (e.g., based on thermodynamic and/or kinetic constants) may be performed. For example, rules (e.g., algorithms) may perform chemical speciation calculations (e.g., based on thermodynamic and/or kinetic constants).

System 350 may include element 364, which may include one or more databases. For example, element 364 may include one or more databases receiving, storing, and/or providing formulation identifiers, calculated values of a property of a chemical composition, and/or equilibrium properties (e.g., based on kinetics and thermodynamic constants).

System 350 may include element 366, which may include one or more databases. For example, element 366 may include one or more databases receiving, storing, and/or providing formulation identifiers and/or testing values (e.g., experimentally determined analytical testing values of a property of a chemical composition). The property of the sample chemical composition may be affected by an interaction two or more of the ingredients of the sample chemical composition. Element 366 may include one or more databases receiving, storing, and/or providing formulation identifiers and/or consumer-derived testing results. Element 366 may include one or more databases receiving, storing, and/or providing formulation identifiers and/or clinical testing results.

At 368, fitting parameters of testing results may be determined. For example, rules (e.g., algorithms) may determine fitting parameters of testing results.

System 350 may include element 370, which may include one or more databases. For example, element 370 may include one or more databases receiving, storing, and/or providing formulation identifiers, aggregated testing results, and/or fitting parameters associated with testing results.

At 358, machine learning information may be determined. For example, rules (e.g., algorithms) may determine machine learning information.

System 350 may include element 360, which may include one or more databases. For example, element 360 may include one or more databases receiving, storing, and/or providing machine learning model parameters.

Figure 4:
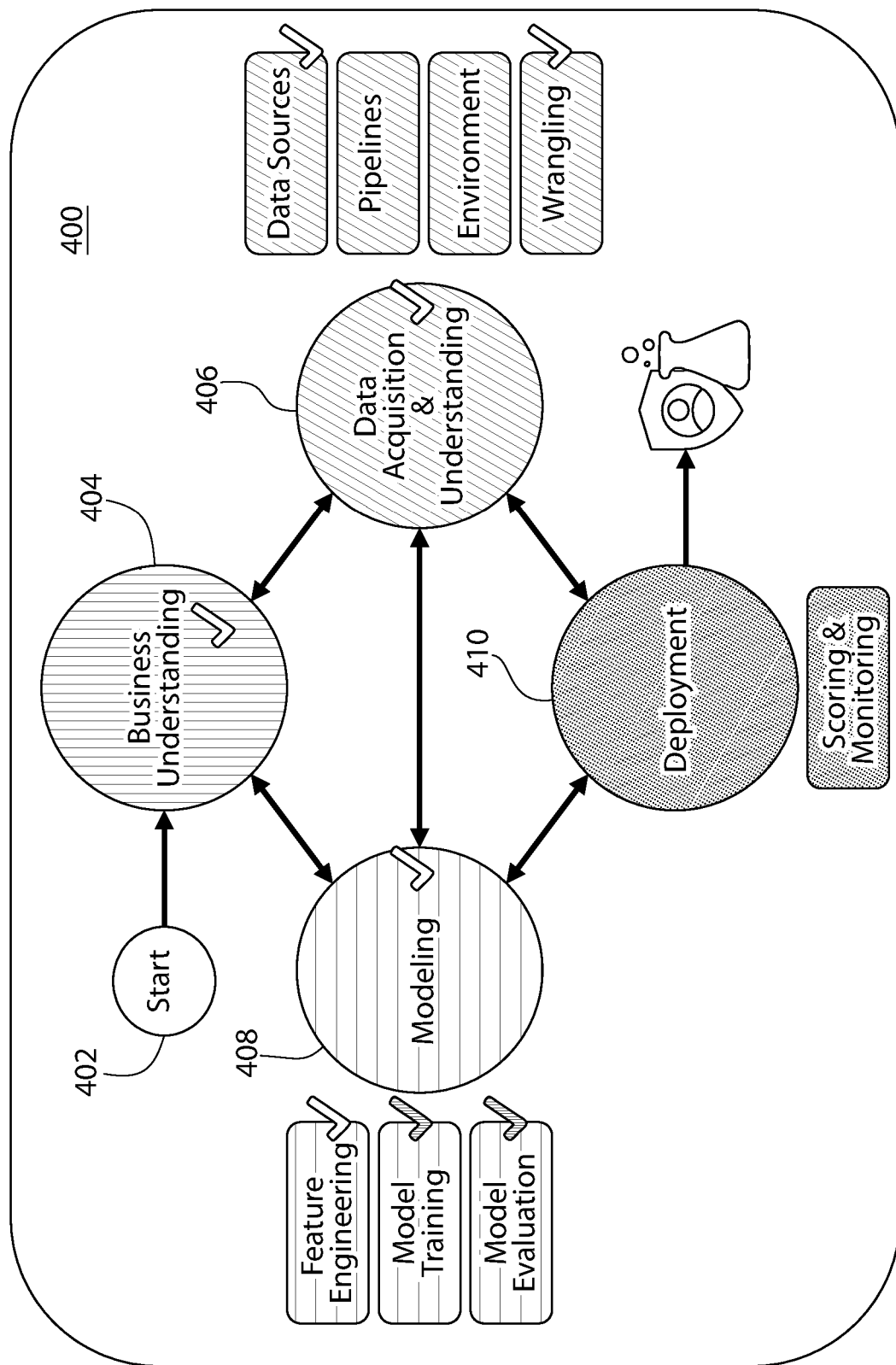
FIG. 4 is another example process for determining a value of a composition using machine learning rules.

FIG. 4 is a process 400 showing other example steps of predicting chemical composition information via machine learning rules, as described herein. Hatch lines are used in FIG. 4 to denote relationships within the process.

At 402, the process begins. At 404, an entity (e.g., a business) may begin to understand and/or improve its understanding of chemical composition information. For example, the entity may begin and/or improve its understanding of a need for chemical compositions to have a feature, such as a chemical composition having a pH of a certain value, an emulsifying purpose, a sweetness, a thickener, etc. Although the entity may understand a need for the chemical composition to have a certain feature (e.g., value), the entity may not know the ingredients of the chemical composition that will create such a feature (e.g., value).

At 406, data relating to the chemical composition may be acquired. For example, the entity may acquire identities (e.g., names, ingredients, chemoinformatic properties, etc.) of chemical compositions, values of properties of chemical compositions, etc. The information of the chemical composition may be acquired via an experimental measurement, a mathematical computation, clinical consumer trials, one or more data sources (e.g., a database, file, etc.), or other informational avenues. An association between the information may be identified and/or determined. For example, an association between an identity of a chemical composition and a value of a property of the chemical composition may be determined.

At 408, a machine learning model may be trained and/or used, as described herein. For example, information relating to a chemical composition (e.g., a sample chemical composition) may be used to train a machine learning model. The information may be an identity of a chemical composition and an associated value of a property of the chemical composition. The trained machine learning model may be used to determine and/or predict a value (e.g., an unknown value) of a chemical composition (such as a considered chemical composition), for example, based on an identity of the chemical composition (e.g., the chemical composition).

At 410, the machine learning model may be deployed. At deployment, the machine learning model may determine a value of a property of a chemical composition (e.g., a considered chemical composition) based on an identity of the chemical composition, may determine an identity of the chemical composition based on a value of a property of a chemical composition, etc.

The determined value of the property of the chemical composition may be compared against a desired value of the property of the chemical composition. For example, the pH value returned from the machine learning model may be compared against a desired pH value. The pH value returned from the machine learning model may be compared against an actual (e.g., actually measured) pH value. If it is determined that the value of the property is the same (e.g., substantially the same) as the desired value, the entity may move towards creating a chemical composition (e.g., a personal care product) having the desired value of the property. The entity may use the ingredients input into the machine learning model to create the chemical composition having the desired value of the property. For example, the entity may create a chemical composition using the ingredients input into the machine learning model that resulted in a determined (e.g., predicted) pH value that is desired. A personal care product may be created using the chemical composition such that the personal care product will be comprised of ingredients resulting in the desired value of the property.

Figure 5:
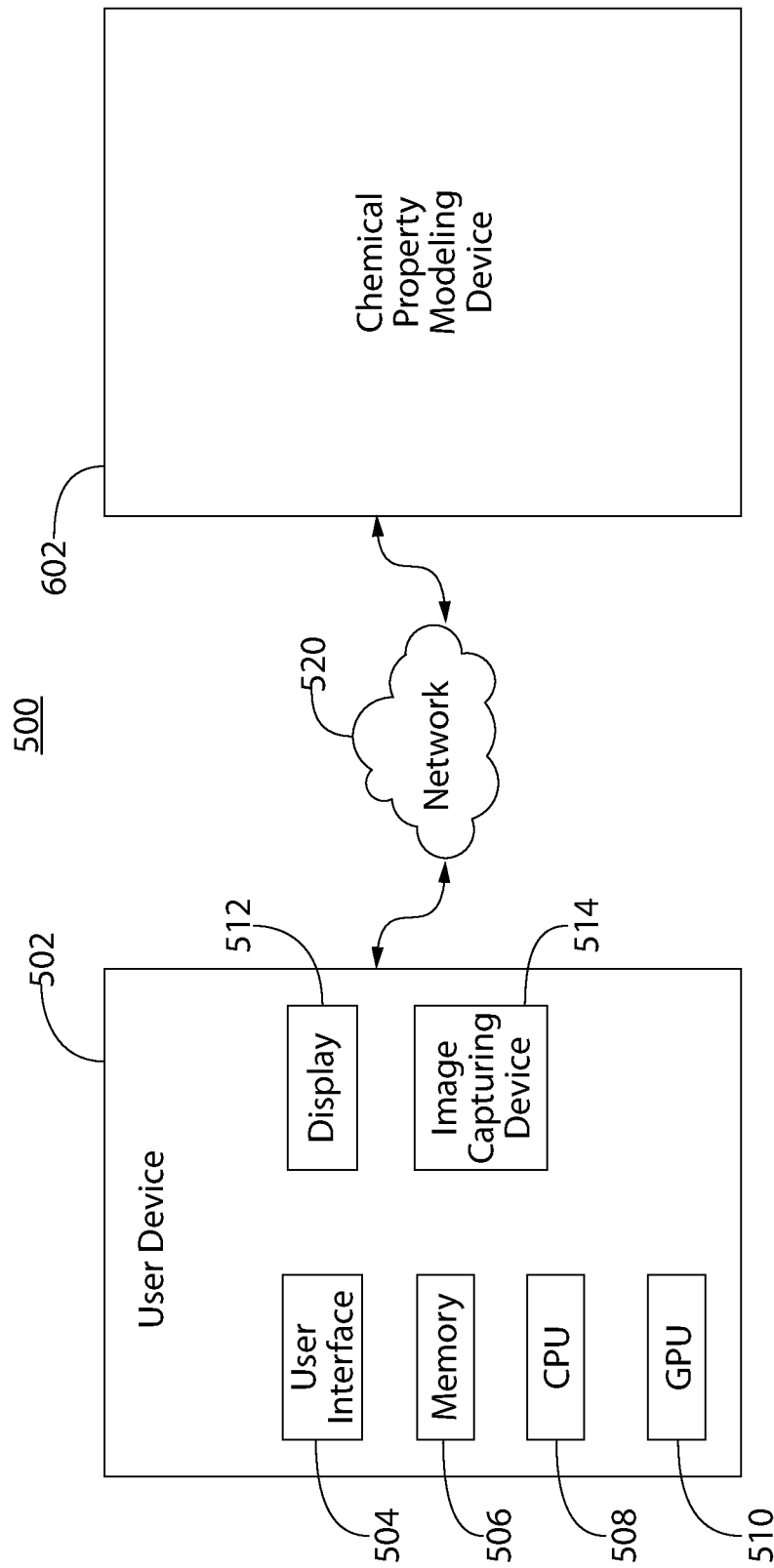
FIG. 5 is a block diagram of an example system including a user device.

FIG. 5 is a block diagram of an example system 500 for determining (e.g., predicting) data associated with a composition (e.g., chemical composition) forming a product, such as a personal care product. Data may include an identity of a chemical composition, a value of a property of a chemical composition, and/or one or more types of data. The data may be determined based on one or more attributes and/or parameters. For example, system 500 may determine (e.g., predict) the data associated with a property of a chemical composition based on one or more attributes/parameters and machine learning techniques. Although examples provided herein may relate to determining (e.g., predicting) an identity of a chemical composition, a value of a property of a chemical composition, and/or a fitting parameter using machine learning techniques, a person of skill in the art will understand that one or more other values and/or parameters relating to a chemical composition may be determined (e.g., predicted) using machine learning techniques. For example, chemoinformatic values of ingredients of a chemical composition may be determined, chemical constants may be determined, consumer perceptions may be determined, etc.

System 500 includes a user device 502 configured to connect to a properties modeling device, such as example chemical properties modeling device 602 (further described in FIG. 6) via a network 520. Network 520 may include wired and/or wireless communication networks. For example, networks 520 may include a local area network (LAN), a metropolitan area network (MAN), and/or a wide area network (WAN). Network 520 may facilitate a connection to the Internet. In further examples, network 520 may include wired telephone and cable hardware, satellite, cellular phone communication networks, etc.

User device 502 may include a user interface 504, a memory 506, a central processing unit (CPU) 508, a graphics processing unit (GPU) 510, an image capturing device 514, and/or a display 512. User device 502 may be implemented as a user equipment (UE) such as a mobile device, a computer, laptop, tablet, desktop, or any other suitable type of computing device.

User interface 504 may allow a user to interact with user device 502. For example, user interface 504 may include a user-input device such as an interactive portion of display 512 (e.g., a "soft" keyboard displayed on display 512), an external hardware keyboard configured to communicate with user device 504 via a wired or a wireless connection (e.g., a Bluetooth keyboard), an external mouse, or any other user-input device. The user interface 504 may allow a user to input, view, etc. one or more pieces of information relating to a chemical composition forming a personal care product.

Memory 506 may store instructions executable on the CPU 508 and/or the GPU 510. The instructions may include machine readable instructions that, when executed by CPU 508 and/or GPU 510, cause the CPU 508 and/or GPU 510 to perform various acts. Memory 506 may store instructions that when executed by CPU 508 and/or GPU 510 cause CPU 508 and/or GPU 510 to enable user interface 504 to interact with a user. For example, executable instructions may enable user interface to display (via Display 512) one or more prompts to a user, and/or accept user input. Instructions stored in memory 506 may enable a user to input an identity of a chemical composition and/or a value of a property of the chemical composition, for example. In other examples, a user may utilize user interface 504 to click, hold, or drag a cursor to define identities, values, and/or properties of a chemical composition.

CPU 508 and/or GPU 510 may be configured to communicate with memory 506 to store to and read data from memory 506. For example, memory 506 may be a computer-readable non-transitory storage device that may include any combination of volatile (e.g., random access memory (RAM)) or non-volatile (e.g., battery-backed RAM, FLASH, etc.) memory.

Image capturing device 514 may be configured to capture an image. The image may be a two-dimensional image, a three-dimensional image, etc. Image capturing device 514 may be configured to capture an image in a digital format having a number of pixels. Although image capturing device 514 is illustrated in FIG. 5 as internal to user device 502, in other examples image capturing device 514 may be internal and/or external to user device 502. In an example, image capturing device 514 may be implemented as a camera coupled to user device 502. Image capturing device 514 may be implemented as a webcam coupled to user device 502 and configured to communicate with user device 502. Image capturing device 514 may be implemented as a digital camera configured to transfer digital images to user device 502 and/or to chemical properties modeling device 602. Such transfers may occur via a cable, a wireless transmission, network 520/620, and/or a physical memory card device transfer (e.g., SD Card, Flash card, etc.), for example. Image capturing device 514 may be used to capture an image of a personal care product, a chemical composition forming the personal care product, data relating to the chemical composition, data relating to one or more features of a personal care product, etc.

In examples the user may input information into the user device 502 relating to one or more compositions (e.g., chemical compositions). The chemical composition information may be transferred to and/or from the chemical property modeling device 602, as shown in FIG. 5. With the chemical property modeling device 602 having information relating to the chemical compositions (e.g., the identities of the chemical compositions and/or the values of the properties of the chemical compositions), the chemical property modeling device 602 may return information about the chemical composition. For example, the chemical property modeling device 602 may provide values (e.g., predicted values) of properties of chemical compositions.

User device 502 may obtain information (e.g., unknown information) about one or more chemical compositions (e.g., names of chemical compositions, ingredients of chemical compositions, chemoinformatic values of ingredients of chemical compositions, values of properties of chemical compositions, etc.) for prediction purposes. For example, a user (e.g., a user of user device 502) may desire to know an identity of a chemical composition having a value (e.g., desired value) of a property of a personal care product. The value of the property may be affected by one or more ingredients of the chemical composition interacting within one another. The value (e.g., desired value) of a property of a personal care product may be a value (e.g., a pH value) of the personal care product, a function of one or more ingredients of the personal care product, a classification of one or more ingredients of the personal care product, a consumer perception of the personal care product, etc.

The user may input one or more types and/or values of chemical composition information (e.g., names, ingredients, chemoinformatic properties, etc.) into the user device 502, for example, to determine information (e.g., other information) about the chemical compositions. The user device 502 may transmit the information to chemical property modeling device 602. In examples all or some of the steps, processes, methods, etc., may be performed by one device or more than one device (e.g., user device or chemical property modeling device). For example, user device 502 may include chemical properties engine 630 in examples. In other examples, chemical property modeling device 602 may be external to user device 502.

In examples in which chemical property modeling device 602 is separate from user device 502, user device 502 may communicate with chemical property modeling device 602 via one or more wired and/or wireless techniques, as described herein. For example, as shown in FIG. 5, user device 502 may communicate with chemical property modeling device 502 via network 520. Network 520 may be the Internet, in some examples. In other examples, as described herein, network 520 may be Wi-Fi, Bluetooth, LAN, etc.

A value of a property (e.g., a desired value of a property) of a chemical composition may be received. The chemical composition in which the value of the property is received and in which the identity of the chemical composition is to be determined by machine learning rules may be referred to as a considered chemical composition. For example, a user may receive a value (e.g., a desired value) of a property of a chemical composition. The user may transfer the value of the property to the chemical property modeling device 602. The value may relate to a property that is affected by one or more ingredients of the chemical composition, such as a pH value, a fluoride stability value, a viscosity value, an abrasion value, a specific gravity value, a consumer perception value, etc.

Based on the value of the property, the chemical property modeling device 602 may provide an identity of a chemical composition that has (e.g., is predicted to have) that value (e.g., or approximately that value) for the property. For example, the chemical property modeling device 602 may provide a name of a composition that has (e.g., is predicted to have) the value, ingredients of a chemical composition that has (e.g., is predicted to have) the value, chemoinformatic values of ingredients of a chemical composition that has (e.g., is predicted to have) the value, etc.

The user may also, or alternatively, provide information related to the chemical composition to determine a value of a property of the chemical composition. For example, the user may input into the chemical property modeling device 602 a name of a composition, ingredients of a chemical composition, chemoinformatic values of ingredients of a chemical composition, consumer perceptions of the chemical composition, etc. Based on the name, ingredient, and/or chemoinformatic information, the chemical property modeling device 602 may determine a value of a property of the chemical composition. For example, based on the name, ingredient, and/or chemoinformatic information, the chemical property modeling device 602 may determine a pH value, a fluoride stability value, a viscosity value, an abrasion value, a specific gravity value, etc., of the chemical composition.

Figure 6:
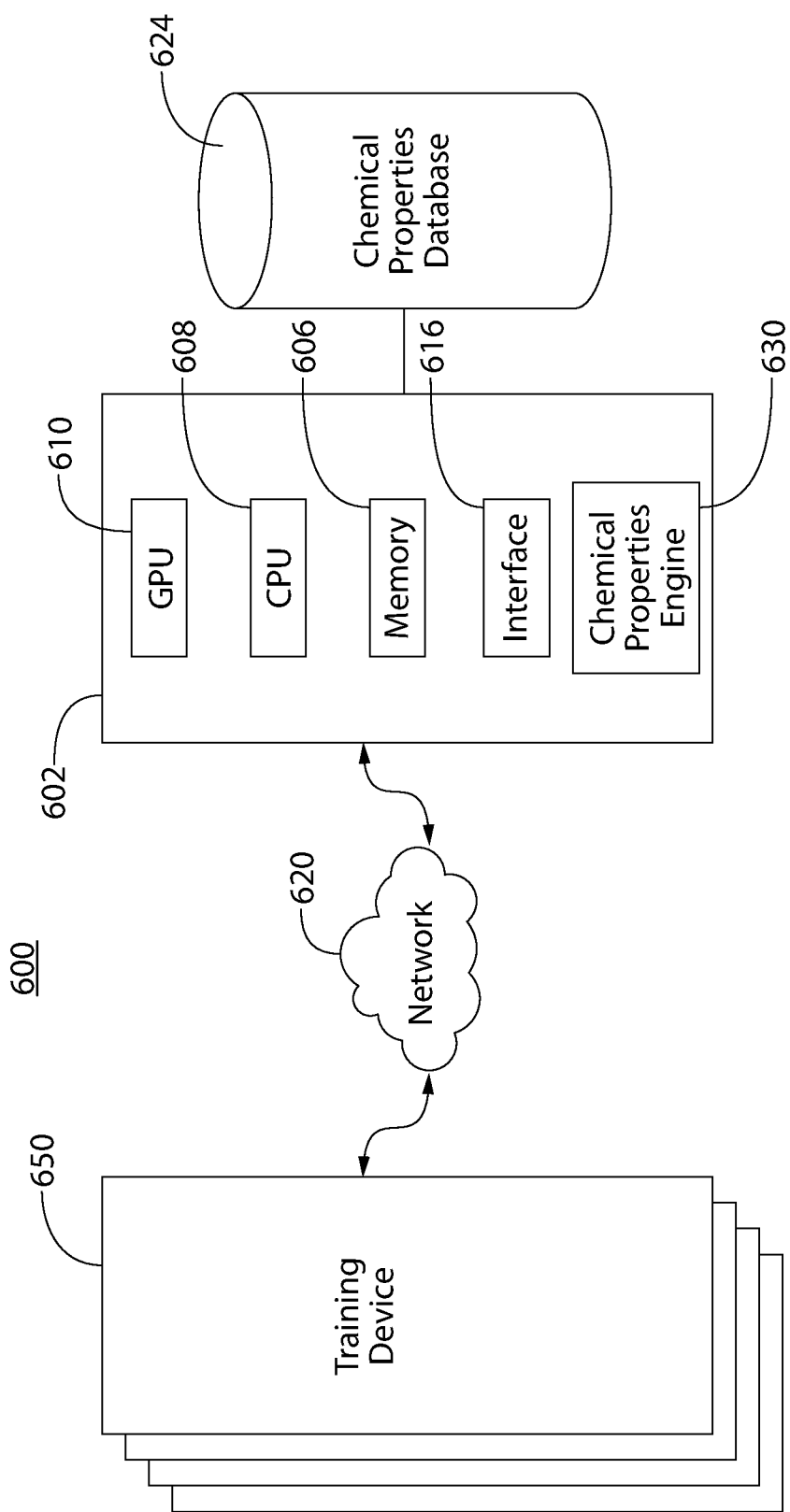
FIG. 6 is a block diagram of an example system including a training of a property engine.

FIG. 6 shows an example system 600 of training a properties engine, such as chemical properties engine 630. Chemical properties engine 630 may be housed in chemical property modeling device 602, although such a configuration is for illustration purposes only. As shown in FIG. 6, training device 650 may communicate with chemical property modeling device 602. For example, training device 650 may communicate with chemical property modeling device 602 via network 620. One or more training devices 650 may provide information to the chemical property modeling device 602, for example, to train the chemical properties engine 630 of chemical property modeling device 602, as described herein.

Training device 650 may provide information to a modeling device, such as chemical property modeling device 602. Information provided to chemical property modeling device 602 may include experimentally measured information relating to a chemical composition (e.g., a chemical composition forming a personal care product), mathematically calculated information relating to a chemical composition, consumer perception information relating to a chemical composition, etc. Training device 650 may provide information relating to chemical compositions that includes identities of chemical compositions (e.g., names of chemical compositions, ingredients of chemical compositions, chemoinformatic values of ingredients of chemical compositions, etc.). The training device 650 may provide values of properties of chemical compositions, such as actual values of properties of chemical compositions and/or mathematically determined values of properties of chemical compositions.

As provided herein, information provided by training device 650 may be based on actual (e.g., actually measured information, such as values of chemical compositions having actually been measured). In addition, or alternatively, information provided by training device 650 may be based on values of the chemical compositions being determined using mathematical calculations, such as thermodynamic calculations of the chemical compositions to determine values of properties of the chemical compositions. Providing this information (e.g., actual information and/or thermodynamically calculated information) to the chemical properties engine 630 may be used to train the model, using machine learning techniques, as described herein. The chemical composition for which information is used to train the machine learning rules may be referred to as a sample chemical composition.

Chemical property modeling device 602 may include a CPU 608, memory 606, GPU 610, interface 616, and chemical properties engine 630. Memory 606 may be configured to store instructions executable on the CPU 608 and/or the GPU 610. The instructions may include machine readable instructions that, when executed by CPU 608 and/or GPU 610, cause the CPU 608 and/or GPU 610 to perform various acts. CPU 608 and/or GPU 610 may be configured to communicate with memory 606 to store to and read data from memory 606. For example, memory 606 may be a computer-readable non-transitory storage device that may include any combination of volatile (e.g., random access memory (RAM), or a non-volatile memory (e.g., battery-backed RAM, FLASH, etc.) memory.

Interface 616 may be configured to interface with one or more devices internal or external to chemical property modeling device 602. For example, interface 616 may be configured to interface with training device 650 and/or chemical properties database 624. Chemical properties database 624 may store information about chemical compositions, such as names of chemical compositions, ingredients of chemical compositions, chemoinformatic values of ingredients of chemical compositions, values of properties of chemical compositions (e.g., pH values, fluoride (e.g., fluoride stability) values, viscosity (e.g., viscosity stability) values, abrasion (e.g., stain removal and dentin abrasion) values, specific gravity values, consumer perception (e.g., sweetness, stickiness, fragrance) values), etc. The information stored within chemical properties database 624 may be used to train the chemical properties engine 630. The information stored within chemical properties database 624 may also, or alternatively, be referenced by chemical properties engine 630 for determining (e.g., predicting) information about a chemical composition (e.g., a considered chemical composition).

A device (e.g., user device 502 and/or chemical property modeling device 602) may receive information of one or more chemical compositions via training device 650 and/or another device. The information may relate to one or more (e.g., many) different types of chemical compositions, a family of chemical compositions, complete and/or incomplete chemical compositions, chemical compositions with extensive history, relatively unknown chemical compositions, etc.

One or more types of information of a chemical composition may be provided to chemical property modeling device 602. For example, one or more types of information of a chemical composition (e.g., sample chemical composition) may be provided to chemical property modeling device 602 to train the chemical property modeling device 602 (e.g., machine learning rules of the chemical property modeling device 602). For example, for a (e.g., each) chemical composition, the chemical property modeling device 602 may receive actual (e.g., actually measured) information of the chemical composition, calculated (e.g., thermodynamically calculated) information of the composition, predicted information of the chemical composition, identity information of the chemical composition, consumer preference information of the chemical composition, etc. The chemical property modeling device 602 may perform an association of the information so that a prediction of chemical composition data (e.g., similar chemical composition data) may be performed.

Chemical property modeling device 602 may use machine learning techniques to develop a software application (e.g., a model). For example, chemical properties engine 630 may include machine learning rules for determining (e.g., predicting) information relating to a chemical composition. Chemical properties engine 630 may include a model (e.g., a machine learning model) to determine (e.g., predict) information regarding a chemical composition. The information provided to the model and/or the information provided by the model may be used to train the model. The information used to train the model may include identities (e.g., names, ingredients, chemoinformatic values of ingredients, etc.) of a chemical composition, values of properties of the chemical composition, consumer perception information of the chemical composition, etc. The information provided to and/or by the model to train the model may relate to chemical compositions (e.g., sample chemical compositions).

The chemical properties engine 630 may include currently known and/or later developed machine learning rules or algorithms. The machine learning rules may be supervised machine learning rules and/or unsupervised machine learning rules. For example, the chemical properties engine 630 may include at least one of a Random Forest rule, Support Vector Machine rule, Naïve Bayes Classification rule, Boosting rule, a variant of a Boosting rule, Alternating Decision Tree rules, Support Vector Machine rules, Perceptron rules, Winnow rules, Hedge rules, rules constructing a linear combination of features or data points, Decision Tree rules, Neural Network rules, logistic regression rules, log linear model rules, Perceptron-like rules, Gaussian process rules, Bayesian techniques, probabilistic modeling techniques, regression trees, ranking rules, Kernel Methods, Margin based rules, linear/quadratic/convex/conic/semi-definite programming techniques, or any modifications of the foregoing.

The chemical properties engine 630 may improve its ability to perform a task as it analyzes more data related to the task. As described herein, the task may be to determine (e.g., predict) unknown information relating to a chemical composition forming a personal care product. The unknown information may be an unknown value of a property of a chemical composition, for example, from known information. For example, the task may be to predict the value of a property of a chemical composition based on identity information of the chemical composition. Conversely, the task may be to predict the identity of a chemical composition based on a value of a property of the chemical composition. In such examples, the more information (relating to one or more chemical compositions) provided to the model, the better the results from the model may be. For example, the model may provide more accurate determinations of values of properties of chemical compositions based on the model receiving numerous pieces of information of the chemical compositions and information related to the identities of the chemical compositions.

As described herein, the machine learning model may be trained using a set of training examples. Each training example may include an example of an object, along with a value for the otherwise unknown property of the object. By processing a set of training examples that include the object and/or the property value for the object, the model may determine (e.g., learn) the attributes or characteristics of the object that are associated with a particular property value. This learning may then be used to predict the property or to predict a classification for other objects. As described herein, machine learning techniques (e.g., rules, algorithms, etc.) may be used to develop models for one or more chemical compositions.

Chemical compositions (and/or one or more ingredients of the chemical compositions) forming a personal care product may be identified and/or classified based on product, function, classification, consumer perception, etc. One or more chemical compositions (and/or one or more ingredients within the chemical compositions) may be identified and/or classified prior to the chemical compositions being input into the machine learning rules. One or more chemical compositions (and/or one or more ingredients within the chemical compositions) may be identified and/or classified by the machine learning rules. For example, machine learning rules may identify and/or classify chemical compositions (and/or one or more ingredients within the chemical compositions) based on product, function, classification, consumer perception, etc.

Models (e.g., machine learning models) may be developed to receive information relating to a chemical composition, for example, to determine (e.g., predict) information of a chemical composition. Training examples (e.g., training sets or training data) may be used to train the chemical properties engine 630. For example, the training data may include the names of sample chemical compositions, ingredients of sample chemical compositions, chemoinformatic values of ingredients of sample chemical compositions, fitting parameters of sample chemical compositions, functions of sample chemical compositions, classifications of sample chemical compositions, values of properties of sample chemical compositions, etc. The values of properties of sample chemical compositions may be determined via calculations, such as via thermodynamic calculations. The values of properties of sample chemical compositions may be determined via an experimental measurement. As described herein, properties of sample chemical compositions may include the pH, fluoride stability, viscosity stability, abrasion, specific gravity, consumer perception properties, etc. of the sample chemical composition.

After training the chemical properties engine 630 (e.g., the machine learning model of chemical properties engine 630) using training data, the chemical properties engine 630 may be used to determine (e.g., predict) data. For example, the chemical properties engine 630 may be used to determine (e.g., predict) parameters that are similar to the parameters used to train the chemical properties engine 630. As an example, chemical properties engine 630 may be trained using identities (e.g. ingredients) of chemical compositions and values of a pH property of chemical compositions. The chemical properties engine 630 may be used to determine unknown values of a pH property, for example, based on the identity (e.g., ingredients) of the chemical composition.

In other examples, after training the chemical properties engine 630 (e.g., the machine learning model of chemical properties engine 630) using training data, the chemical properties engine 630 may be used to determine parameters that are different than the parameters used to train the chemical properties engine 630. As an example, chemical properties engine 630 may be trained using identities (e.g. ingredients) of chemical compositions and values of a pH property of chemical compositions. The chemical properties engine 630 may be used to determine unknown values of a soluble zinc property. The chemical properties engine 630 may be used to determine unknown values of a soluble zinc property based on the identity (e.g., ingredients) of the chemical composition. The different parameters may have a relationship with one another. The relationship between the different parameters may allow the chemical properties engine 630 to predict the different parameters. Using the example above, although the pH property and the soluble zinc property are different properties, there may be a relationship with the pH property and the soluble zinc property that allows the chemical properties engine 630 to predict the soluble zinc data based on pH training data.

Other data related to a chemical composition may be used to train the chemical properties engine 630. For example, data related to a property may be used to train the chemical properties engine 630. As an example, the data related to the property may be a fitting parameter associated with the value of the property, although other types of data may be used to train the chemical properties engine 630. As an example, training data may include an identity (e.g., a name, ingredients, and/or chemoinformatic values of ingredients) of sample chemical compositions and fitting parameters of sample chemical compositions.

A fitting parameter may be used to determine a value of a parameter at a defined instance. For example, the fitting parameter may relate to the rate at which a value changes over time. The fitting parameter may be used to determine a value of a parameter at a future date, day, time, time period, etc. A fitting parameter may be used to define continuous functions. A fitting parameter may be used to determine a value of a property at one or more (e.g., any) point in time. For example, if a value of fluoride stability has been measured at 4, 8, and 13 weeks, a fitting parameter may be derived which may provide values (e.g., expected values) of fluoride stability at intermediate timepoints between 4, 8, and 13 weeks and/or at extended points beyond 13 weeks.

Determining a value of a property at a future date, day, time, time period, etc. may be useful as manufacturers of products (e.g., personal care products) may be required to demonstrate that a product (e.g., personal care product) maintains a minimum threshold quantity of a property throughout the shelf-life of the product. For example, as shelf lives of a product may be on the order of several years, it may be impractical to test products (e.g., new products) at certain time periods (e.g., months, years, etc.) to determine the viability of the products. It may be useful to collect data (e.g., collect data over a short period of time) and use a fitting parameter to extrapolate the value of the property at a longer period of time. Such a model (e.g., a model which predicts fitting parameters) may predict properties at timepoints for which there may be no experimental data.

As an example, a chemical properties engine 630 may be trained using data related to a chemical composition. As described herein, the data may be an identity (e.g., ingredients) of the chemical composition as well as other data. For example, the chemical properties engine 630 may be trained using ingredients of chemical compositions, molecular weights of the ingredients (e.g., each ingredient), weight percentages of the ingredients (e.g., each ingredient), etc. The weight percentages of the ingredients (e.g., each ingredient) may be converted to a molar concentration. The chemical properties engine 630 may be trained using molar concentrations, theoretical total fluoride content, and/or soluble fluoride after aging of a chemical composition (e.g., after aging of a chemical composition for 13 weeks at 40 degrees Celsius). After training the chemical properties engine 630 (e.g., the machine learning model of chemical properties engine 630) using training data, the chemical properties engine 630 may be used to determine (e.g., predict) data. For example, the chemical properties engine 630 may be used to determine (e.g., predict) a value for soluble fluoride after aging, based on an identity (e.g., ingredients) of a chemical composition and/or based on molecular concentration data related to the chemical composition.

A fitting parameter may be used to determine a value of a parameter at a future time period. For example, the chemical properties engine 630 may be trained using ingredients of chemical compositions, molecular weights of the ingredients (e.g., each ingredient), weight percentages of the ingredients (e.g., each ingredient), and/or the fitting parameter. After training the chemical properties engine 630 (e.g., the machine learning model of chemical properties engine 630) using ingredients of chemical compositions, molecular weights of the ingredients (e.g., each ingredient), weight percentages of the ingredients (e.g., each ingredient), and/or the fitting parameter, the chemical properties engine 630 may be used to determine the fitting parameter. The fitting parameter may be used with a fitting function to determine a defined instance, as described herein. For example, the chemical properties engine 630 may be used to determine (e.g., predict) a value of a fitting parameter that can be used with a fitting function to determine the theoretical total fluoride content and/or the soluble fluoride content measured after aging of a chemical composition (e.g., after aging of a chemical composition at 4, 8, and/or 13 weeks at 40 degrees Celsius). Example fitting functions may include an exponential function, polynomial function, power function, trigonometric function, although other fitting functions may be used.

Information included in the training data may be selected and/or input into the model of chemical properties engine 630 based on a function and/or classification. For example, a chemical composition and/or an ingredient of a chemical composition may have a defined function and/or classification, such as an ingredient in a chemical composition having a binding function, a preserving function, a whitening function, an alcohol classification, an ethers classification, etc. The function may relate to how one or more of the ingredients of the chemical composition are used in product form. The function may relate to a pellicle cleaning ratio (PCR) and/or a relative dentin abrasivity (RDA). PCR is a measurement of stain removal and may represent the cleaning efficacy of a personal care product, such as a toothpaste. RDA is a measurement of abrasivity (e.g., pure abrasivity) and may represent the erosive capability of a personal care product, such as a toothpaste. Example functions 700 of a chemical composition and/or an ingredient within the chemical composition may be found in FIG. 7. Example classifications 800 of a chemical composition and/or an ingredient within the chemical composition may be found in FIG. 8. Although FIG. 7 and FIG. 8 provide a list of functions and classifications, respectively, it should be understood by those of skill in the art that the functions provided in FIG. 7 and the classifications are provided in FIG. 8 are for example purposes only and are non-limiting.

In examples, one or more chemical compositions may (e.g., may only) be input into a model if the chemical compositions have a function (e.g., a desired function). As an example, a set may consist of eighty chemical compositions. Of the eighty chemical compositions, fourteen chemical compositions may include an ingredient that provides a function of whitening. A user may desire to determine a value of a property of a chemical composition wherein the chemical composition (e.g., an ingredient of the chemical composition) may have a whitening function. In such an example, the model may be trained using (e.g., only using) chemical compositions (e.g., ingredients of the chemical composition) having a whitening function, such as the fourteen chemical compositions in the above example. Also, or alternatively, the model may categorize (e.g., automatically categorize, dynamically categorize, etc.) chemical compositions based on the function of the chemical composition.

With the model including (e.g., only including) chemical compositions of a defined function, or the model categorizing chemical compositions based on a defined function, the chemical properties engine 630 may provide information of a chemical composition having (e.g., only having) the function. For example, the chemical properties engine 630 may determine a value of a property of a chemical composition having a function (e.g., a flavoring function, a binding function, etc.) based on an identity of the chemical composition. Conversely, the chemical properties engine 630 may determine an identity of a chemical composition having a function based on a value of a property of the chemical composition.

In other examples, one or more chemical compositions may (e.g., may only) be input into a model if the chemical compositions have a classification (e.g., a chemical classification). The classification may relate to molecular properties of an ingredient of a chemical composition, such as a chemical composition forming a personal care product. The chemical compositions may (e.g., may only) be input into a model if the chemical compositions have a desired classification. Example chemical classifications may include an alcohols classification, an amino acids classification, an enzymes classification, a fatty acids classification, a ketones classification, peptides classification, as well as other classifications provided in FIG. 8.

As an example, a set may consist of forty chemical compositions. Of the forty chemical compositions, ten chemical compositions may include an ingredient that is classified as an ether. A user may desire to determine a value of a property of a chemical composition wherein the chemical composition (e.g., an ingredient of the chemical composition) may have a classification of an ether. In such an example, the model may be trained using (e.g., only using) chemical compositions (e.g., ingredients of the chemical composition) having a classification of an ether. Also, or alternatively, the model may categorize (e.g., automatically categorize, dynamically categorize, etc.) chemical compositions based on the classifications of the chemical composition.

With the model including (e.g., only including) chemical compositions of a defined classification, or the model categorizing chemical compositions based on a defined classification, the chemical properties engine 630 may provide information of a chemical composition having (e.g., only having) the classification. For example, the chemical properties engine 630 may determine a value of a property of a chemical composition having a classification (e.g., an alcohols classification, a fatty acids classifications, etc.) based on an identity of the chemical composition. Conversely, the chemical properties engine 630 may determine an identity of a chemical composition having a classification based on a value of a property of the chemical composition.

As described herein, information relating to one or more chemical compositions may be input into the model based on a function, classification, consumer perception, etc., of the chemical composition and/or ingredient of the chemical composition. Information (e.g., identities, values of properties, etc.) of chemical compositions may be identified based on experimentation, simulation, mathematical computations, analysis, clinical consumer trials, and/or assumptions regarding the property being modeled. For example, actual (e.g. actually measured) values of properties of chemical compositions may be identified and input into the model.

A training set (e.g., identities of chemical compositions and associated values of properties of the chemical compositions) may be used to train a machine learning model (e.g., chemical properties engine 630). The machine learning model (e.g., chemical properties engine 630) may perform a selected machine learning rule or algorithm using the training set, as described herein. Once trained, the model may be used to determine (e.g., predict) the identity and/or values of properties of the chemical composition, relative to the property of interest.

Figure 9A:
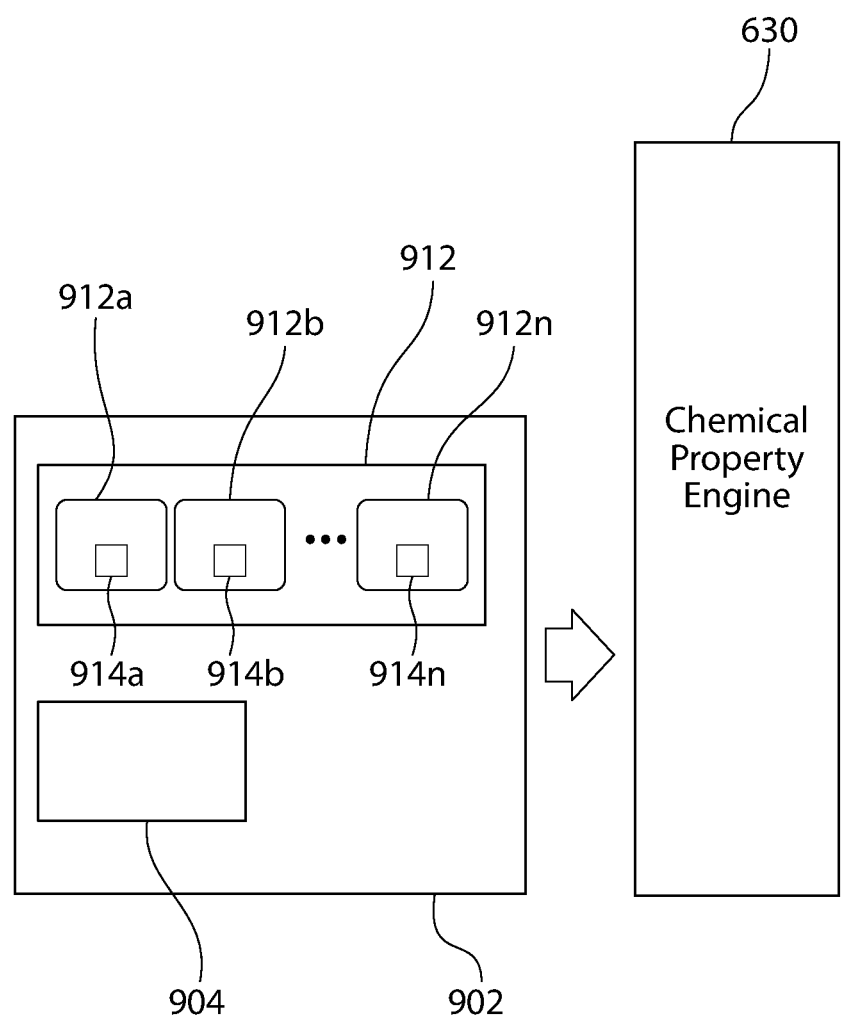
FIGS. 9A, 9B, 9C are block diagrams of an example training of a machine learning model and receiving values from the machine learning model.

FIG. 9A shows a block diagram of example data used for training chemical properties engine 630. Data 902 may relate to one or more chemical compositions (e.g., sample chemical compositions). Data 902 may be known and/or determined. For example, data 902 may be known by experimentally measuring the data, mathematically calculating (e.g., via thermodynamic calculations) the data, receiving the data from storage (e.g., from a database, such as a chemical properties database 624), receiving the data from clinical trials, etc. Data 902 may include values for one or more parameters. For example, data 902 may include identities of chemical compositions. Identities may include the names of the chemical compositions, ingredients of the chemical compositions, chemoinformatic values/properties of the ingredients of the chemical compositions, values of properties of the chemical compositions, consumer perceptions of the chemical compositions, etc. Data may be input into the chemical properties engine 630, for example, to train the model to predict one or more values of chemical compositions.

As shown in FIG. 9A, data 902 may include one or more ingredients 912 of one or more chemical compositions.

Ingredients may include a first ingredient 912a, a second ingredient 912b, etc. Example ingredients are provided in FIGS. 1A, 1B and 2A, 2B. For example, a chemical composition may include water, glycerin, propylene glycol, and flavor ingredients. In such example, data 902 may include data for water, glycerin, propylene glycol, and flavor ingredients. Each ingredient 912a, 912b, etc., may include an identity of the ingredient and/or a chemoinformatic value for the ingredient. For example, data 902 may include chemoinformatic values 914a, 914b, etc. In the example chemical composition that includes glycerin, propylene glycol, and flavor ingredients, each of glycerin, propylene glycol, and flavor will have a respective chemoinformatic value within data 902.

Data 902 may include a value 904 of a property of the chemical composition. The value 904 of the property may be affected by one or more of the ingredients. For example, the value 904 of the property may be affected by one or more of the ingredients interacting with one or more other ingredients of the chemical composition. A property may be pH, fluoride stability, viscosity stability, abrasion, specific gravity, a consumer perception of the chemical composition, etc. Data 902 may include a value of the property, such as a value of a pH property. As described herein, the value of the property (e.g., pH property) may be affected by one or more of the ingredients of the chemical composition.

One or more values of data 902 may be input into the chemical properties engine 630, for example, to train the chemical properties engine 630. Identities of chemical compositions and associated values of properties (e.g., other properties) of the chemical compositions may be input into the chemical properties engine 630. As an example, ingredients of chemical composition (e.g., sample chemical composition) and associated values of parameters may be input into the chemical properties engine 630. The chemical properties engine 630 may provide an association of the ingredients of the chemical compositions and the values of parameters of the chemical compositions.

Figure 9B:
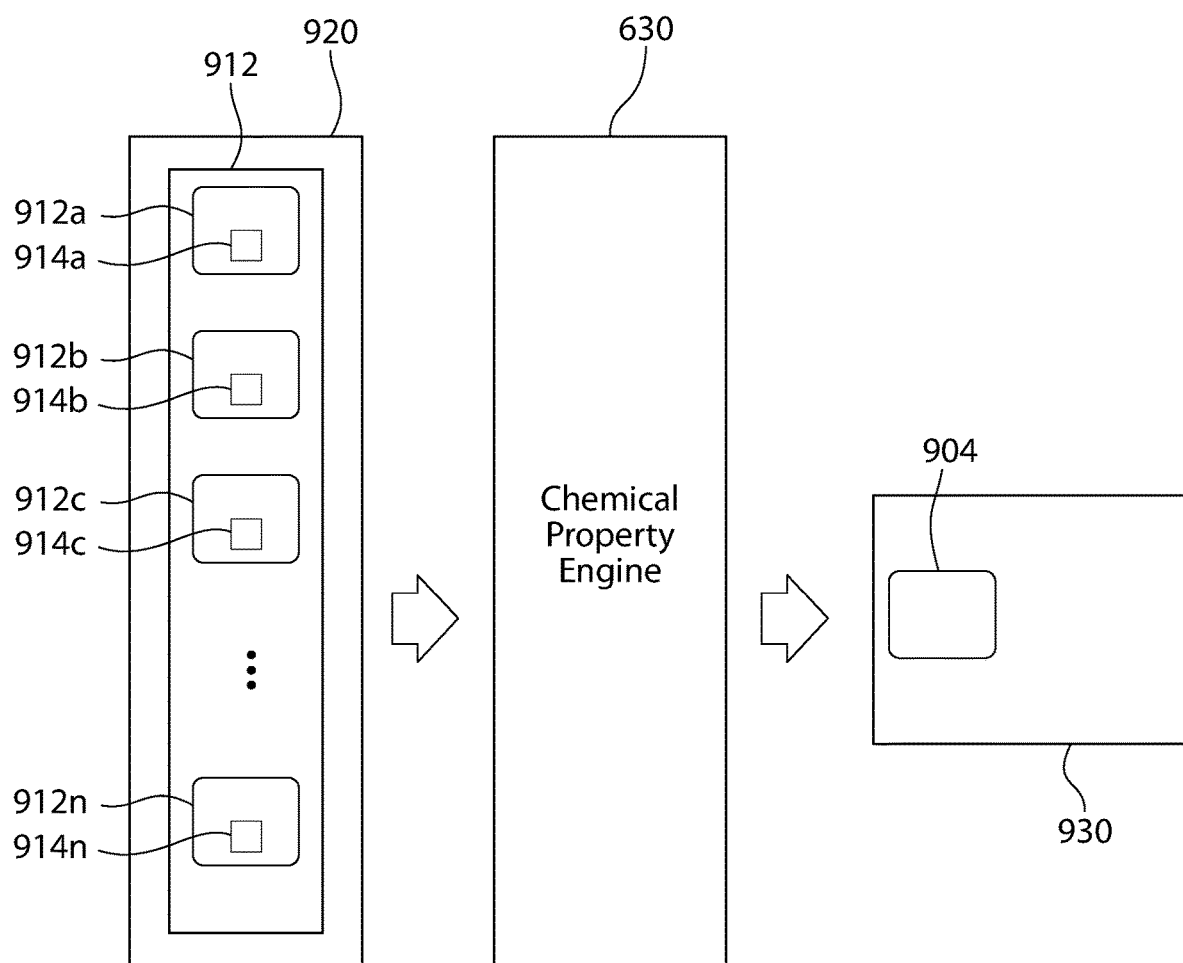

FIG. 9B shows a block diagram of example data 920 used for determining information relating to a chemical composition using chemical properties engine 630. For example, FIG. 9B shows a block diagram of example data 920 used for determining a value of a property via chemical properties engine 630. Data 920 may relate to one or more chemical compositions (e.g., considered chemical compositions). Data 920 may be known and/or determined. For example, data 920 may be known and/or determined by receiving the data from storage (e.g., from a database, such as a chemical properties database 624), experimentally measuring the data, mathematically calculating (e.g., via thermodynamic calculations) the data, etc. Data 920 may include values for one or more parameters. Data 920 may include identities of chemical compositions, such as the names of the chemical compositions, ingredients of the chemical compositions, chemoinformatic values/properties of the ingredients of the chemical compositions, values of properties of the chemical compositions, etc. Data 920 may be input into the chemical properties engine 630, for example, to determine from the chemical properties engine 630 (e.g., machine learning model of chemical properties engine 630) one or more values of properties of chemical compositions.

Data 920 may include one or more ingredients 912 of one or more chemical compositions. Ingredients may include a first ingredient 912a, a second ingredient 912b, etc. For example, a chemical composition may include water, glycerin, propylene glycol, and flavor ingredients. In such example, data 920 may include data for water, glycerin, propylene glycol, and flavor ingredients. Each ingredient 912a, 912b, etc., may include a chemoinformatic value for the ingredient. For example, data 902 may include chemoinformatic values 914a, 914b, etc. In the example chemical composition that includes glycerin, propylene glycol, and flavor ingredients, each of glycerin, propylene glycol, and flavor will have a respective chemoinformatic value within data 920.

One or more values of data 902 may be input into the chemical properties engine 630, for example, to determine (e.g., determine from the chemical properties engine 630) a value of a property of the chemical composition. For example, ingredients of a chemical composition (e.g., a sample chemical composition) may be input into the chemical properties engine 630. The chemical properties engine 630 may run (e.g., process) one or more machine learning rules to determine a value of a property of the chemical composition. The chemical properties engine 630 may provide the value of the property of the chemical composition after determining the value.

Chemical properties engine 630 (e.g., model of chemical properties engine 630) may be configured to predict a value of a property of the chemical composition, for example, based on receiving identities of ingredients of a chemical composition, etc. In an example, the values of the properties of the chemical composition may be affected by ingredients of the chemical composition (e.g., may be affected by an interaction of one or more of the ingredients of the chemical composition). When information relating to a chemical composition is supplied to the trained model, the output may comprise a prediction regarding the value of the property of the chemical composition, a fitting parameter associated with the chemical composition, identities of the chemical composition, etc. The property may relate to a pH of the chemical composition, a viscosity stability of the chemical composition, an abrasion of the chemical composition, a specific gravity of the chemical composition, a consumer perception of the chemical composition, etc. The predictions may take the form of a value from a continuous range of values or from a discrete value, for example.

Figure 9C:
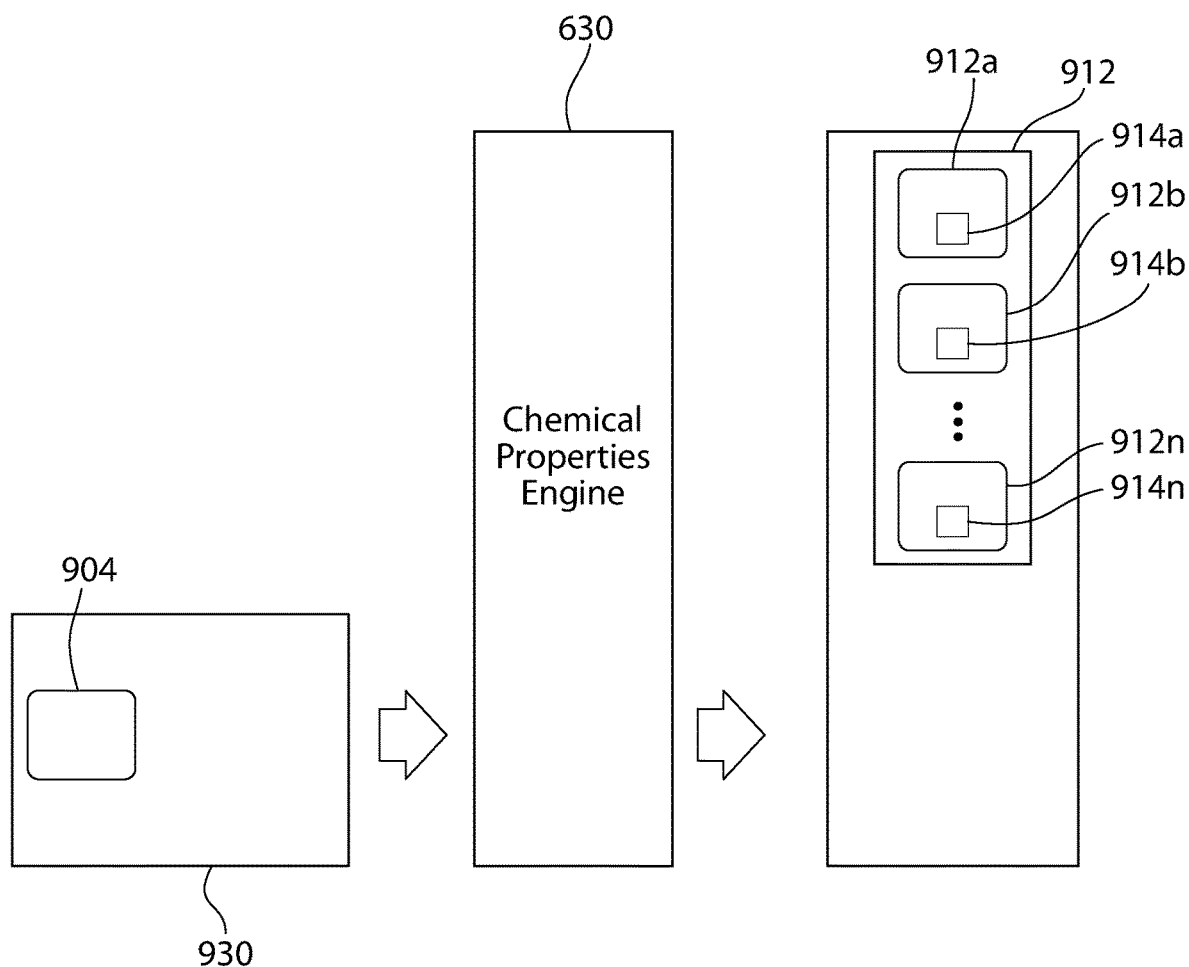

FIG. 9C shows a block diagram of example data 930 used for determining an identity of a chemical composition via chemical properties engine 630. Data 930 may relate to one or more chemical compositions (e.g., considered chemical compositions). Data 930 may be known. For example, as described herein, data 930 may be known by experimentally measuring the data, mathematically calculating (e.g., via thermodynamic calculations) the data, receiving the data via a clinical consumer trial, receiving the data from storage (e.g., from a database, such as a chemical properties database 624), etc. As shown in FIG. 9C, data 930 may include a value 904 of a property of a chemical composition, etc. Data 930 may be input into the chemical properties engine 630, for example, to determine information (e.g., associated information) of chemical compositions. For example, data 930 (e.g., value 904) may be input into the chemical properties engine 630, for example, to determine from the model ingredients 912 of the chemical composition determined (e.g., predicted) to relate to the value 904 of the property input into the chemical properties engine 630.

As described herein, data 930 may include a value 904 of a property. The value 904 of the property may be input into chemical properties engine 630, for example, to predict (e.g., determine) a name of a chemical composition, one or more ingredients 912 of a chemical composition, chemoinformatic values 914a, 914b, . . . , 914n of a chemical composition, etc. Ingredients may include a first ingredient 912a, a second ingredient 912b, etc. For example, a chemical composition may include water, glycerin, propylene glycol, and flavor ingredients. A chemoinformatic value may be associated with an (e.g., each) ingredient 912a, 912b, etc. For example, ingredient 912a may include chemoinformatic value 914a.

As an example, a value 904 of a property of the chemical composition may be input into chemical properties engine 630. Based on value 904 of the property of the chemical composition, the chemical properties engine 630 (e.g., model of chemical properties engine 630) may be configured to predict identities (e.g., names, ingredients, chemoinformatic values, etc.) of a chemical composition forming a personal care product. When information relating to a chemical composition is supplied to the chemical properties engine 630, the output may comprise a determination (e.g., prediction) regarding the identities (e g., names, chemoinformatic values, etc.) of a chemical composition forming the personal care product, a fitting parameter associated with the chemical composition, a value (e.g., another value) of a property of the chemical composition, etc. The chemical properties engine 630 may provide the names, ingredients, chemoinformatic values, etc. of the chemical composition to user via user device 502, for example.

Figure 10C:
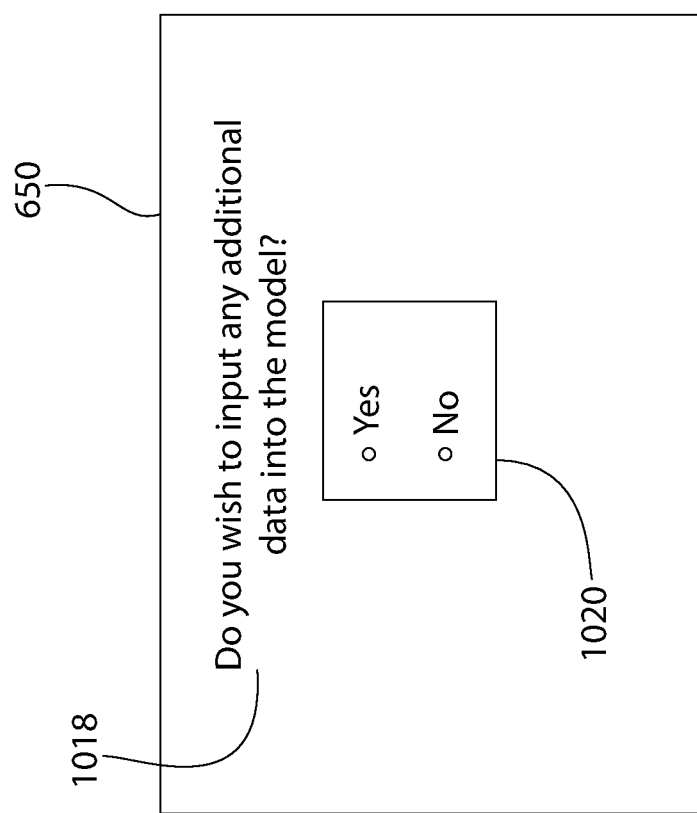

FIGS. 10A-10C show example graphical user interfaces (GUIs) for training a chemical properties modeling device 602 (e.g., a chemical properties engine 630 within chemical properties modeling device 602). The GUI may be displayed on one or more devices. For example, the GUI may be displayed on a training device, such as training device 650, a user device, etc.

As shown in FIG. 10A, the GUI may request information from the user, for example, the GUI may request information from the user via prompt request 1010. Prompt request 1010 may ask the user what data the user would like to use to train the chemical properties engine 630 (e.g., model of chemical properties engine 630). The data used to train the model may be referred to as sample data. The data may include an identity (e.g., name, ingredients, chemoinformatic values of ingredients) of a chemical composition forming a personal care product, a value of a property of personal care product, etc. The GUI may provide an input mechanism 1012 for the user to provide a response to prompt request 1010. For example, the GUI may have a text box for receiving text from the user, a radio button for selection, etc. As shown in FIG. 10A, check box 1012 may be provided. In examples in which a text box is provided, the user may check one or more of the data in the input mechanism 1012 for training the chemical properties engine 630.

After the user selects the data desired to be input into the chemical properties engine 630 (e.g., for training the chemical properties engine 630), the user may input such data. The user may input the data manually (e.g., via manually typing or speaking the data). The user may input a single piece of data or the user may input multiple pieces of data. For example, as shown in FIG. 10B, GUI may provide an indication for the user to select the data to be input into the chemical properties engine 630. The GUI may display the data to be input into the chemical properties engine 630, For example, the GUI may display the data to be input into the chemical properties engine 630 based on the input provided on input mechanism 1012 of FIG. 10A.

In an example, the user may desire to input ingredients 1016a of a chemical composition forming a personal care product and a value 1016b of a property of the chemical composition. As shown in FIG. 10B, the user may select a file to provide the ingredient information (via Browse 1017a) and the value (via Browse 1017b) of the property information. Although FIG. 10B shows a Browse button for inputting data, one of skill in the art will understand that other methods exist for selecting and/or inputting data into chemical properties engine 630, such as via a database (such as a database housed on a server, such as a cloud server), via one or more hard drives, via external devices (such as user device 502), etc.

The user may input data into the chemical properties engine 630 for one or more chemical compositions. For example, the user may train the chemical properties engine 630 with data relating to tens, hundreds, thousands, etc., of chemical compositions. The user may train the chemical properties engine 630 with the same data for one or more of the chemical compositions. For example, the user may train the chemical properties engine 630 with ingredients and values of properties of dozens of chemical compositions.

The user may train the chemical properties engine 630 with different data (e.g., types of data) for one or more of the chemical compositions. For example, the user may train the chemical properties engine 630 with ingredients and values of properties for some of the chemical compositions, with chemoinformatic values and values of properties for some of the chemical compositions, with names of chemical compositions and values of properties for some of the chemical compositions, etc. The user may train the chemical properties engine 630 with values of properties comprising a pH, a fluoride stability, a viscosity stability, an abrasion, a specific gravity, consumer perceptions, etc. The training device 650 (e.g., GUI of training device) may request if the user desires to input additional data. For example, as shown in FIG. 10C, the GUI may provide an additional data prompt 1018 asking the user if the user desires to input any additional data into the chemical properties engine 630 (e.g., the model of chemical properties engine 630). The user may desire to input additional data into chemical properties engine 630 if the user desires to further train the chemical properties engine 630. If the user desires to input additional data into the chemical properties engine 630, the user may select the Yes prompt in area 1020, otherwise the user may select the No prompt in area 1020. If the user selects the Yes prompt in area 1020, the GUI shown in FIG. B (and described herein) may be provided to the user. If the user selects the No prompt in area 1020, the user may exit the GUI.

FIGS. 11A-11D show example graphical user interfaces (GUIs) for determining (e.g., predicting) data from a chemical properties modeling device 602 (e.g., a chemical properties engine 630 within chemical properties modeling device 602). The GUI may be displayed on one or more devices. For example, the GUI may be displayed on a user device, such as user device 502.

As shown in FIG. 11A, the GUI may request information from the user, for example, via prompt request 1110. Prompt request 1110 may ask the user what data the user would like the model to determine (e.g., predict). The GUI may provide an input mechanism 1112 for the user to provide a response to prompt request 1110. For example, the GUI may have a text box for receiving text from the user, a radio button for selection, etc. As shown in FIG. 11A, check box 1112 may be provided. The user may check one or more of the data in the input mechanism 1112 so that the chemical properties engine 630 may determine one or more pieces of data relating to the chemical composition. Input mechanism may permit additional information, including sub-categories of information, to be selected for determination. For example, input mechanism 1112 may allow a user to further define the value of the property to be determined to be one a pH, a fluoride stability, a viscosity stability, an abrasion, a specific gravity, a consumer perception, etc.

After the user selects what data the user desires the chemical properties engine 630 to determine, the user may input data that is associated with the desired data, as shown in FIG. 11B. For example, prompt 1116 indicates that the user desires to determine a value of a property of the chemical composition (based on the user's input at input 1112, in FIG. 11A). As shown in FIG. 11B, the GUI may provide input 1118, allowing the user to select what data the user desires to input into the chemical properties engine 630, for example, to determine the value of the property of the chemical composition. Examples of data to be input into the chemical properties engine 630 includes identity (e.g., name, ingredients, chemoinformatic values of ingredients) data of a chemical composition forming a personal care product, a value of a property of personal care product, etc.

After the user selects the data that the user desires to determine (1112), and the data that the user would like to use to determine the value of the personal care product (1118), the user may provide the associated data. FIG. 11C shows an example GUI in which user may at input data, at 1122. Prompt 1120 indicates that the user has chosen to input ingredients of the chemical composition (to determine a value of a property of the chemical composition), however such indication is for illustration purposes only and other types of data may be provided by user to determine information relating to chemical composition.

The user may input the data manually (e.g., via manually typing or speaking the data). For example, the user may input the ingredients of the chemical composition, as shown on FIG. 11C, manually. The user may input a single piece of data or the user may input multiple pieces of data. For example, as shown in FIG. 11C, GUI may provide an indication for the user to select the data to be input into the chemical properties engine 630. The user may select a file to provide the ingredient information (via Browse button 1122). Although FIG. 11C shows a Browse button 1122 for inputting data, one of skill in the art will understand that other methods exist for selecting and/or inputting data into chemical properties engine 630, such as via a database (such as a database housed on the cloud), via external hard drives, via external devices (such as user device 502), etc.

The GUI may provide the determined (e.g., predicted) data. For example, the GUI may provide the value of a parameter, as shown in FIG. 11D. The value of the parameter may relate to a chemical composition forming a personal care product. Prompt 1130 may display the associated data provided by the user. For example, prompt 1130 may display that the determined data is based on the ingredient information (e.g., the ingredient information provided by the user). Prompt 1130 may indicate what data has been determined. For example, prompt 1130 indicates that the value of the property of the personal care product is being determined. Output 1132 provides the determined value. As shown on FIG. 11D, the determined value may be 1.7. In examples the GUI may provide further information of the information such as that the property is a pH, a fluoride stability, a viscosity stability, an abrasion, a specific gravity, and/or a consumer perception.

Figure 12:
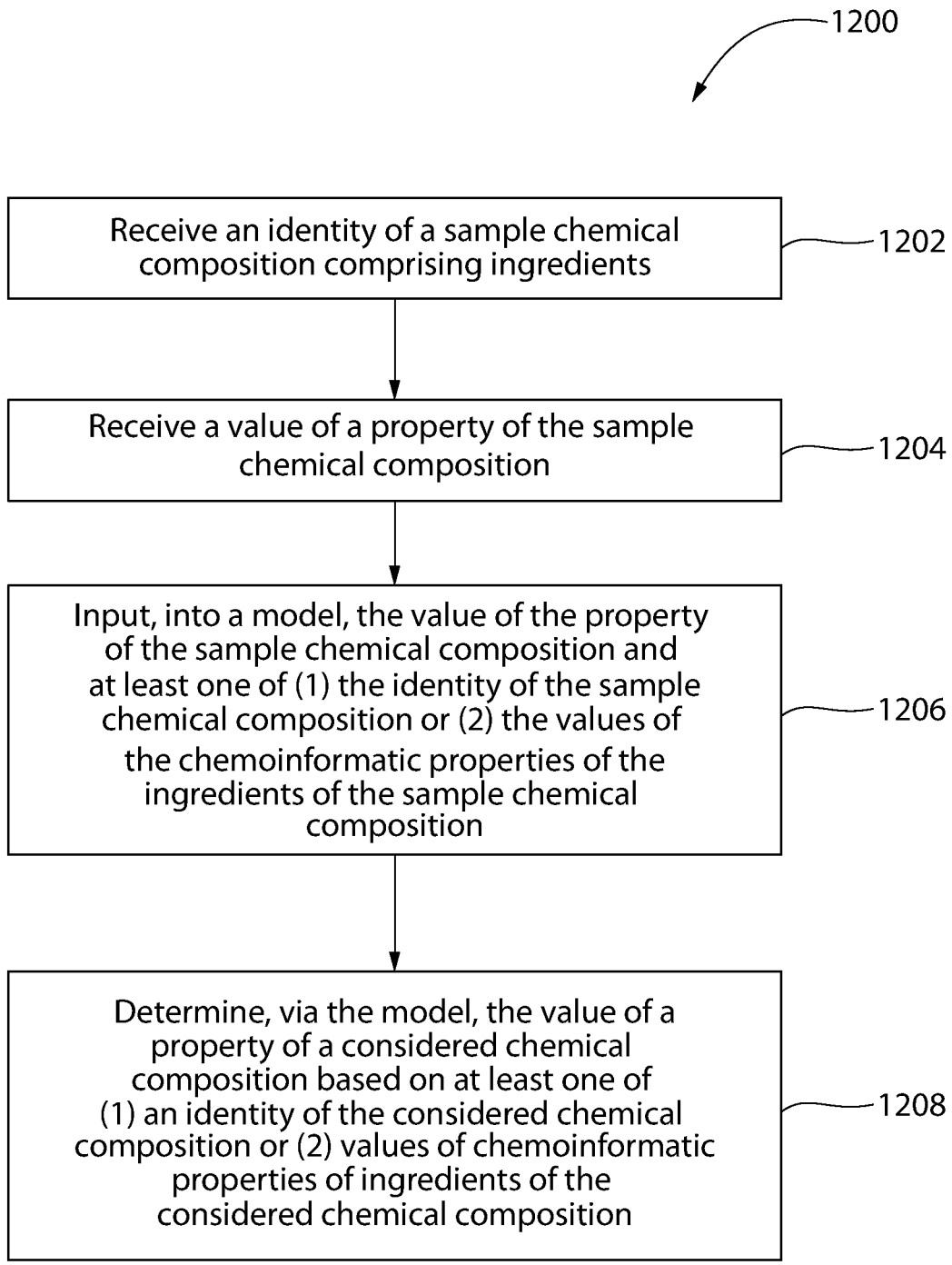
FIG. 12 is an example method of determining values of a composition, as described herein.

FIG. 12 is an example process 1200 for determining (e.g., predicting) a value of a chemical composition. The value may be an identity of a chemical composition, such as a name of the chemical composition, ingredients of the chemical composition, chemoinformatic values of ingredients of the chemical composition, a value of a property of the chemical composition, etc.

At 1202, an identity of a chemical composition (e.g., a sample chemical composition) may be received. The identity may be received from a database or another storage device, a described herein. As provided above, the identity of the chemical composition may be a name of the chemical composition, ingredients of the chemical composition, chemoinformatic values of ingredients of the chemical composition, etc.

At 1204, a value of a parameter of the chemical composition (e.g., a sample chemical composition) may be received. The value of the property may be affected by one or more ingredients of the chemical composition. As an example, the property may be a pH of the chemical composition, and the value of the property may be the value of the pH of the chemical composition.

The identity of the chemical composition (e.g., the sample chemical composition) and/or the value of the parameter may be used to train a machine learning model, as described herein. For example, at 1206 the value of the property of the chemical composition (e.g., the sample chemical composition) may be input into the machine learning model to train the machine learning model. An identity of the chemical composition may be input into the machine learning model to train the machine learning model. The identity of the chemical composition may be one or more of a name of the chemical composition, ingredients of the chemical composition, chemoinformatic values of ingredients of the chemical composition, etc. The machine learning model may make associations of the value of the property of the chemical composition and the identity of the chemical composition.

After the machine learning model is trained, the machine learning model may determine one or more values of a chemical composition. The machine learning model may determine one or more values of a chemical composition in response to receiving an associated piece of data. For example, the machine learning model may determine a value of a property of a chemical composition based on an identity of the chemical composition, such as ingredients of the chemical composition or a name of the chemical composition. The property of the chemical composition may be a pH value of the chemical composition, a fluoride stability value of the chemical composition, a viscosity value of the chemical composition, an abrasion value of the chemical composition, a specific gravity value of the chemical composition, a consumer perception value of a chemical composition, etc.

For example, at 1208 the machine learning model may receive one or more values of a chemical composition (e.g., a considered chemical composition). As described herein, a considered chemical composition may be a chemical composition in which one or more values are unknown and desired to be known. For example, an identity of a considered chemical composition may be known, ingredients of the considered chemical composition may be known, and/or chemoinformatic values of the considered chemical composition may be known. The value of a property of the considered chemical composition may be unknown.

The known values (e.g., the identity of the considered chemical composition, ingredients of the considered chemical composition, and/or chemoinformatic values of the considered chemical composition) may be input into the machine learning model. Based on the values input into the machine learning model, the machine learning model may determine a value of a property of the considered chemical composition. The value of the considered chemical composition may be displayed or otherwise provided to a user.

In examples, the user may determine whether the value of the property corresponds to a desired value of the property. For example, it may be desired (e.g., required) that a personal care product have a defined value for a property of the personal care product. The value may relate to a pH value or one or more other properties described herein. If the machine learning model determines that a chemical composition has a value of the property that aligns with a desired value of the property, the user may perform an action, such as producing a personal care product having the ingredients associated with the determined value. In other examples, the user may perform actions to confirm that the results provided by the machine learning model are accurate, such as by performing a measurement of the value of the property, performing mathematically calculations of the value. The user may confirm that the results provided by the machine learning model are accurate before producing a personal care product having the ingredients associated with the determined value.

Systems described herein may be implemented using any available computer system and adaptations contemplated for known and later developed computing platforms and hardware. Further, the methods described herein may be carried out by software applications configured to execute on computer systems ranging from single-user workstations, client server networks, large distributed systems employing peer-to-peer techniques, or clustered grid systems. In an example, a high-speed computing cluster may be used. The computer systems used to practice the methods described herein may be geographically dispersed across local or national boundaries using a data communications network such as the Internet. Moreover, predictions generated at one location may be transported to other locations using well known data storage and transmission techniques, and predictions may be verified experimentally at the other locations.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A computer-implemented method of determining a value of a property of a considered chemical composition, the method comprising:
    inputting, into a model, an identity of the considered chemical composition, wherein the considered chemical composition comprises ingredients, each of the ingredients of the considered chemical composition being associated with a value of a chemoinformatic property of chemoinformatic properties of the considered chemical composition; wherein the model is trained by receiving an identity of a sample chemical composition and a value of a property of the sample chemical composition, the value of the property of the sample chemical composition being identified via at least one of an experimental measurement of the sample chemical composition or a thermodynamic calculation of the sample chemical composition;
    determining, via the model, a value of the property of the considered chemical composition based on the identity of the considered chemical composition, wherein the value of the property of the considered chemical composition is affected by an interaction of at least two of the ingredients of the considered chemical composition; and
    producing a personal care product comprised of the considered chemical composition;
    wherein the inputting and determining steps are performed by one or more processors.

2. The method according to claim 1, wherein the property of the considered chemical composition comprises at least one of a pH, a rheology, an abrasivity, a chemical degradation, a phase change, a turbidity, an ingredient solubility, a volatile loss, or a consumer perception.

3. The method according to claim 1, wherein the identity of the considered chemical composition comprises identities of the ingredients of the considered chemical composition.

4. The method according to claim 1, wherein the model is a machine learning model and the value of the property of the considered chemical composition is determined via rules of the machine learning model.

5. The method according to claim 4, wherein the machine learning model comprises a supervised learning approach.

6. The method according to claim 1, wherein the property of the considered chemical composition relates to a physiochemical property of the considered chemical composition, the physiochemical property relating to a physical property or a chemical property of the considered chemical composition.

7. The method according to claim 1, wherein the property of the considered chemical composition is identical to a property of the sample chemical composition used to train the model.

8. The method according to claim 1, wherein the personal care product comprised of the considered chemical composition is a toothpaste.

9. The method according to claim 1, wherein the chemoinformatic property of the considered chemical composition relates to at least one of a qualitative category, a qualitative sensory attribute, a molecular formula, an acid dissociation constant, a solubility product, a structural topology, a functional group count, a chemical fragment count, a hydrophobicity, a partition coefficient, a steric parameter, an association constant, or a hydrophile lipophile balance (HLB).

10. The method according to claim 9, wherein the qualitative category comprises at least one of an ingredient function or an ingredient classification.

11. A computer-implemented method of determining a fitting parameter value of a considered chemical composition, the method comprising:
    inputting, into a machine learning model, at least one of an identity of the considered chemical composition or values of chemoinformatic properties of ingredients of the considered chemical composition, wherein each of the ingredients of the considered chemical composition is associated with a value of a chemoinformatic property of chemoinformatic properties of the considered chemical composition; wherein the machine learning model is trained by receiving an identity of a sample chemical composition and a value of a fitting parameter associated with a value of a property of the sample chemical composition, the value of the property of the sample chemical composition being affected by an interaction of at least two of the ingredients of the sample chemical composition;
    determining, via the machine learning model, the fitting parameter value of the considered chemical composition based on at least one of an identity of the considered chemical composition or values of chemoinformatic properties of ingredients of the considered chemical composition, wherein the fitting parameter value of the considered chemical composition is associated with a value of a property of a considered chemical composition, the property of the considered chemical composition being affected by an interaction of at least two of the ingredients of the considered chemical composition; and producing a personal care product comprised of the considered chemical composition;

wherein the inputting and determining steps are performed by one or more processors.

12. The method according to claim 11, further comprising:

determining the value of the property of the considered chemical composition at an instance based on (1) an identity of the instance, (2) the fitting parameter value of the considered chemical composition, and (3) a fitting function.

13. The method according to claim 11, wherein the instance is a future time period.

14. The method according to claim 12, wherein the fitting function comprises at least one of an exponential function, polynomial function, power function, or trigonometric function.

15. A computer-implemented method of determining an identity of a considered chemical composition, the method comprising:

inputting, into a model, at least one of values of chemoinformatic properties of ingredients of the considered chemical composition or a value of a property of the considered chemical composition, wherein the value of the property of the considered chemical composition is affected by an interaction of at least two of the ingredients of the considered chemical composition;

wherein the model is trained by receiving values of chemoinformatic properties of ingredients of a sample chemical composition and a value of a property of the sample chemical composition;

determining, via the model, the identity of the considered chemical composition based on the at least one of the values of the chemoinformatic properties of the ingredients of the considered chemical composition or the value of the property of the considered chemical composition; and producing a personal care product comprised of the identified considered chemical composition;

wherein the inputting and determining steps are performed by one or more processors.

16. The method of claim 15, wherein the determining of the identity of the considered chemical composition is based on the value of the property of the considered chemical composition and not based on the values of the chemoinformatic properties of the ingredients of the considered chemical composition.

17. The method of claim 15, wherein each of the ingredients of the considered chemical composition has a respective chemoinformatic property.

18. The method according to claim 17, wherein the chemoinformatic property of each of the ingredients of the considered chemical composition relates to at least one of a qualitative category, a qualitative sensory attribute, a molecular formula, an acid dissociation constant, a solubility product, a structural topology, a functional group count, a chemical fragment count, a hydrophobicity, a partition coefficient, a steric parameter, an association constant, or a hydrophile lipophile balance (HLB).

19. The method of claim 15, wherein the model is a machine learning model relating to a supervised learning approach.

20. The method of claim 15, wherein the personal care product comprised of the considered chemical composition is a toothpaste.

* * * * *